（12）United States Patent
Nadzadi et al.

(10) Patent No.: US 10,219,908 B2
(45) Date of Patent: Mar. 5, 2019

(54) FEMORAL COMPONENT FOR BONE CONSERVATION

(71) Applicant: MAKO Surgical Corp., Fort Lauderdale, FL (US)

(72) Inventors: Mark Nadzadi, Memphis, TN (US); Jason Otto, Plantation, FL (US); Amit Mistry, Fort Lauderdale, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 112 days.

(21) Appl. No.: 14/578,007

(22) Filed: Dec. 19, 2014

(65) Prior Publication Data

US 2015/0182343 A1 Jul. 2, 2015

Related U.S. Application Data

(60) Provisional application No. 61/921,964, filed on Dec. 30, 2013.

(51) Int. Cl.
*A61F 2/38* (2006.01)
*A61B 17/16* (2006.01)
(Continued)

(52) U.S. Cl.
CPC ........ *A61F 2/3859* (2013.01); *A61B 17/1675* (2013.01); *A61B 34/30* (2016.02); *A61B 34/37* (2016.02); *A61F 2002/30878* (2013.01)

(58) Field of Classification Search
CPC .......... A61F 2/3859; A61F 2002/30878; A61F 2002/2828
See application file for complete search history.

(56) References Cited

U.S. PATENT DOCUMENTS 6,972,039 B2 * 12/2005 Metzger ................ A61F 2/3868
623/20.29
D622,854 S 8/2010 Otto et al.
(Continued)

FOREIGN PATENT DOCUMENTS

EP 0707839 A1 * 4/1996 ........... A61F 2/3859

OTHER PUBLICATIONS

International Search Report and Written Opinion for PCT Application No. PCT/US2014/071675, dated Jun. 10, 2015, 15 pages.
(Continued)

*Primary Examiner* — David H Willse
*Assistant Examiner* — Javier Blanco
(74) *Attorney, Agent, or Firm* — Lerner, David, Littenberg, Krumholz & Mentlik, LLP

(57) ABSTRACT

A femoral prosthetic component includes a patellar guide portion, a pair of condyles projecting from the guide portion and forming an intercondylar notch therebetween, a bearing surface, and an interface surface configured to face a resected surface of a femur. The interface surface comprises an anterior face and a posterior face, and is substantially contoured between the anterior and posterior face to match a contoured surface of the femur. The substantially contoured interface surface may include at least one planar surface portion to abut a flat cut portion in the surface of the femur. This planar surface portion may be a distal flat at a distal face of the interface surface. The contoured interface surface may alternatively include a plurality of planar surface portions. The femoral prosthetic component is configured such that preparation of the bone to match the interface surface results in minimal resection of the distal femur.

7 Claims, 26 Drawing Sheets

(51) Int. Cl.
*A61B 34/30* (2016.01)
*A61B 34/37* (2016.01)
*A61F 2/30* (2006.01)

(56) References Cited

U.S. PATENT DOCUMENTS

| | | | |
|---|---|---|---|
| D625,415 S | 10/2010 | Otto et al. | |
| D626,234 S | 10/2010 | Otto et al. | |
| 7,842,092 B2 | 11/2010 | Otto et al. | |
| 8,475,535 B2 | 7/2013 | Otto | |
| 8,702,803 B2 | 4/2014 | Otto et al. | |
| 8,911,501 B2 | 12/2014 | Irwin et al. | |
| 8,977,021 B2 | 3/2015 | Kang et al. | |
| 2007/0135925 A1* | 6/2007 | Walker | A61F 2/3859 623/20.21 |
| 2008/0004701 A1 | 1/2008 | Axelson et al. | |
| 2008/0058945 A1 | 3/2008 | Hajaj et al. | |
| 2008/0058948 A1* | 3/2008 | Biegun | A61F 2/3859 623/20.35 |
| 2008/0097615 A1* | 4/2008 | Lipman | A61F 2/3886 623/20.27 |
| 2008/0262812 A1 | 10/2008 | Arata et al. | |
| 2009/0204221 A1 | 8/2009 | Walker | |
| 2010/0094429 A1 | 4/2010 | Otto | |
| 2010/0153076 A1 | 6/2010 | Bellettre et al. | |
| 2010/0153081 A1 | 6/2010 | Bellettre et al. | |
| 2010/0217400 A1 | 8/2010 | Nortman et al. | |
| 2011/0066079 A1 | 3/2011 | Otto et al. | |
| 2012/0041566 A1* | 2/2012 | Lenz | A61F 2/38 623/23.42 |
| 2012/0310617 A1 | 12/2012 | Bellettre et al. | |
| 2013/0172783 A1 | 7/2013 | Ikits et al. | |
| 2013/0173008 A1 | 7/2013 | Bechtold et al. | |
| 2014/0180290 A1 | 6/2014 | Otto et al. | |
| 2014/0188134 A1 | 7/2014 | Nortman et al. | |
| 2014/0189508 A1 | 7/2014 | Granchi et al. | |

OTHER PUBLICATIONS

Invitation to Pay Additional Fees for PCT Application No. PCT/US2014/071675, dated Mar. 25, 2015, 6 pages.
U.S. Appl. No. 14/578,064, filed Dec. 19, 2014, MAKO Surgical Corp.
U.S. Appl. No. 14/579,730, filed Dec. 22, 2014, MAKO Surgical Corp.
U.S. Appl. No. 14/640,895, filed Mar. 6, 2015, MAKO Surgical Corp.
U.S. Appl. No. 14/640,919, filed Mar. 6, 2015, MAKO Surgical Corp.
U.S. Appl. No. 29/329,712, filed Dec. 19, 2008, Otto.
U.S. Appl. No. 29/329,715, filed Dec. 19, 2008, Otto.
U.S. Appl. No. 29/466,144, filed Sep. 4, 2013, MAKO Surgical Corp.
U.S. Appl. No. 29/466,147, filed Sep. 4, 2013, MAKO Surgical Corp.
U.S. Appl. No. 29/466,148, filed Sep. 4, 2013, MAKO Surgical Corp.

* cited by examiner

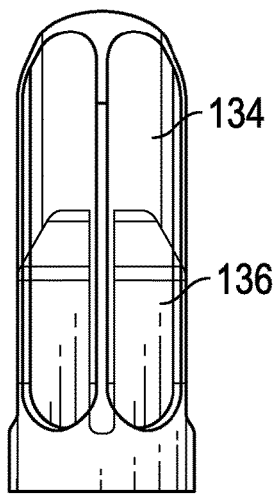 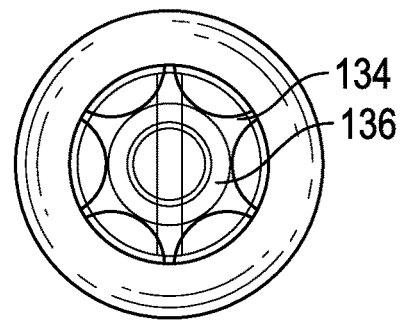
FIG. 19A  FIG. 19B
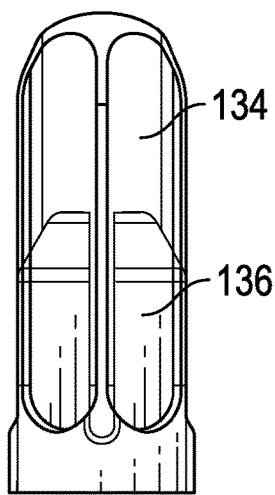 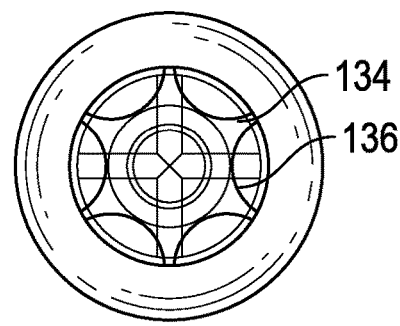
FIG. 20A  FIG. 20B

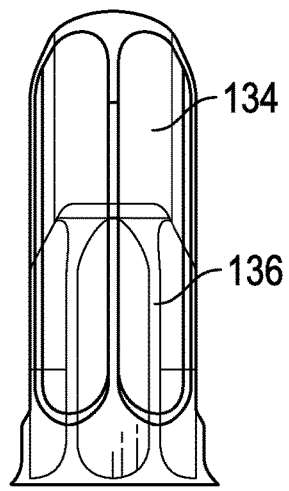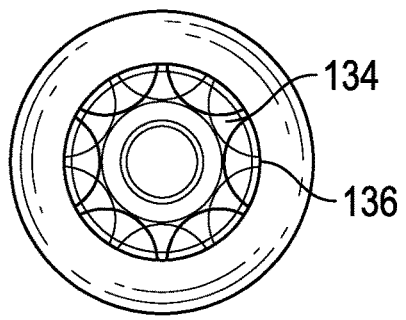
FIG. 21A  FIG. 21B
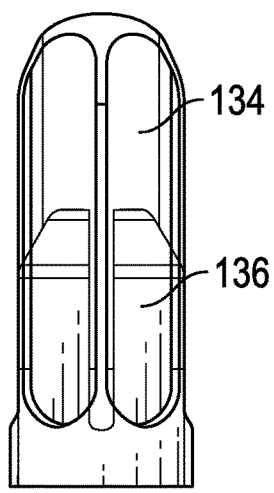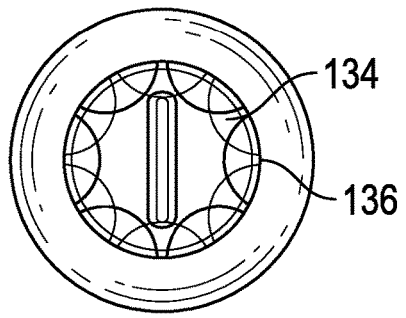
FIG. 22A  FIG. 22B

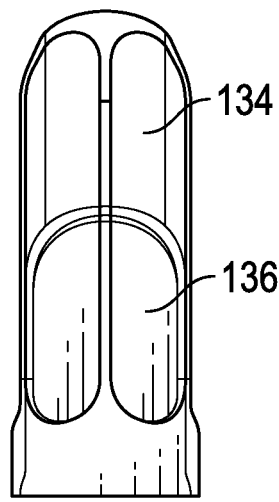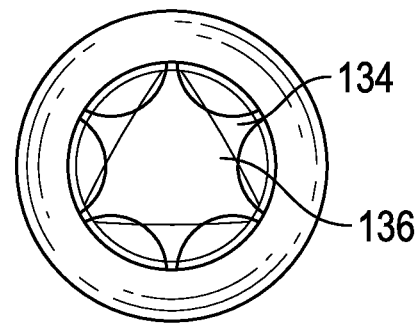
FIG. 23A            FIG. 23B
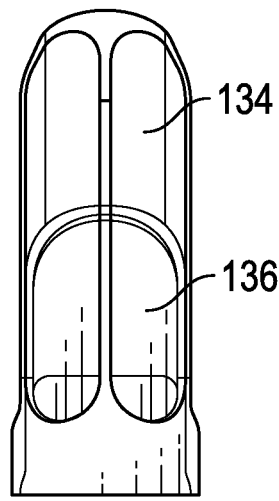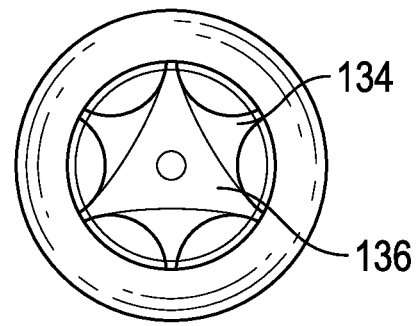
FIG. 24A            FIG. 24B

FEMORAL COMPONENT FOR BONE CONSERVATION

CROSS-REFERENCE TO RELATED APPLICATIONS

This application claims the benefit of and priority to U.S. Provisional Patent Application Ser. No. 61/921,964, filed Dec. 30, 2013, the disclosure of which is hereby incorporated by reference in its entirety.

BACKGROUND

The present invention relates generally to orthopedic prosthesis systems used in knee joint replacement surgeries and, more particularly, to a femoral implant for use in knee arthroplasty procedures.

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint.

In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

One knee replacement procedure—total knee arthroplasty ("TKA")—involves the resection of some or all of each of the medial and lateral condyles of both the femur and tibia and the removal of the fibro-cartilage menisci located at the femorotibial interface. A prosthetic femoral component, typically made of titanium or other strong, surgical-grade metal, is fitted and secured to the distal end of the femur to replace the resected portion of the femur. Similarly, a prosthetic tibial component, the base of which is also typically made of titanium or other suitable metal, is fitted and secured to the proximal end of the tibia to replace the resected portion of the tibia.

Femoral components commonly utilize a bone facing surface having a five-cut or five-surface baseline configuration, such as that depicted in FIGS. 2A-2C. These designs are typically not directed to patient-specific anatomy and use relatively basic lines and arcs for reduced cost manufacture. Designs of this type can be generally used on many patients having unique knee joint anatomies, and scaled only in size to accommodate the particular patient. Though advantageous for manufacture, the five basic cut design may require a high amount of bone volume to be removed in preparation to receive the implant thereon, thereby significantly reducing the strength of the bone.

SUMMARY

A femoral prosthetic component includes a patellar guide portion, a pair of condyles projecting from the guide portion and forming an intercondylar notch therebetween, a bearing surface, and an interface surface configured to face a resected surface of a femur. The interface surface comprises an anterior face and a posterior face, and is substantially contoured between the anterior and posterior face to match a contoured surface of the femur. The substantially contoured interface surface may include at least one planar surface portion to abut a flat cut portion in the surface of the femur. This planar surface portion may be a distal flat at a distal face of the interface surface. The contoured interface surface may alternatively include a plurality of planar surface portions. The femoral prosthetic component may be configured such that preparation of the bone to match the interface surface results in minimal resection of the distal femur.

Another embodiment of the invention relates to a prosthetic component includes a prosthetic body portion, the body portion having a bearing surface and an interface surface configured to face a resected surface of a bone prepared to receive the prosthetic component. The interface surface is substantially contoured to match a contoured surface of the prepared bone and the contoured interface surface is configured such that preparation of the bone to receive the prosthetic component results in minimal bone resection.

Yet another embodiment of the invention relates to a method for implanting a prosthetic implant including selecting a prosthetic component, wherein the prosthetic component comprises a prosthetic body portion, the body portion having a bearing surface and an interface surface configured to face a resected surface of a bone prepared to receive the prosthetic component. The method further includes removing, using a first cutting tool, a first portion of the bone to form a resected surface of the bone configured to match a counterpart portion of the interface surface of the prosthetic component. The interface surface of the prosthetic component is substantially contoured and is configured to match the resected surface of the bone that is substantially contoured.

The invention is capable of other embodiments and of being practiced or being carried out in various ways. Alternative exemplary embodiments relate to other features and combinations of features as may be generally recited in the claims.

BRIEF DESCRIPTION OF THE FIGURES

The invention will become more fully understood from the following detailed description, taken in conjunction with the accompanying drawings, wherein like reference numerals refer to like elements, in which:

FIG. 19A illustrates a side view of a first embodiment of a trial projection.

FIG. 19B illustrates a top view of the first embodiment of a trial projection.

FIG. 20A illustrates a side view of a second embodiment of a trial projection.

FIG. 20B illustrates a top view of the second embodiment of a trial projection.

FIG. 21A illustrates a side view of a third embodiment of a trial projection.

FIG. 21B illustrates a top view of the third embodiment of a trial projection.

FIG. 22A illustrates a side view of a fourth embodiment of a trial projection.

FIG. 22B illustrates a top view of the fourth embodiment of a trial projection.

FIG. 23A illustrates a side view of a fifth embodiment of a trial projection.

FIG. 23B illustrates a top view of the fifth embodiment of a trial projection.

FIG. 24A illustrates a side view of a sixth embodiment of a trial projection.

FIG. 24B illustrates a top view of the sixth embodiment of a trial projection.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figure 1:
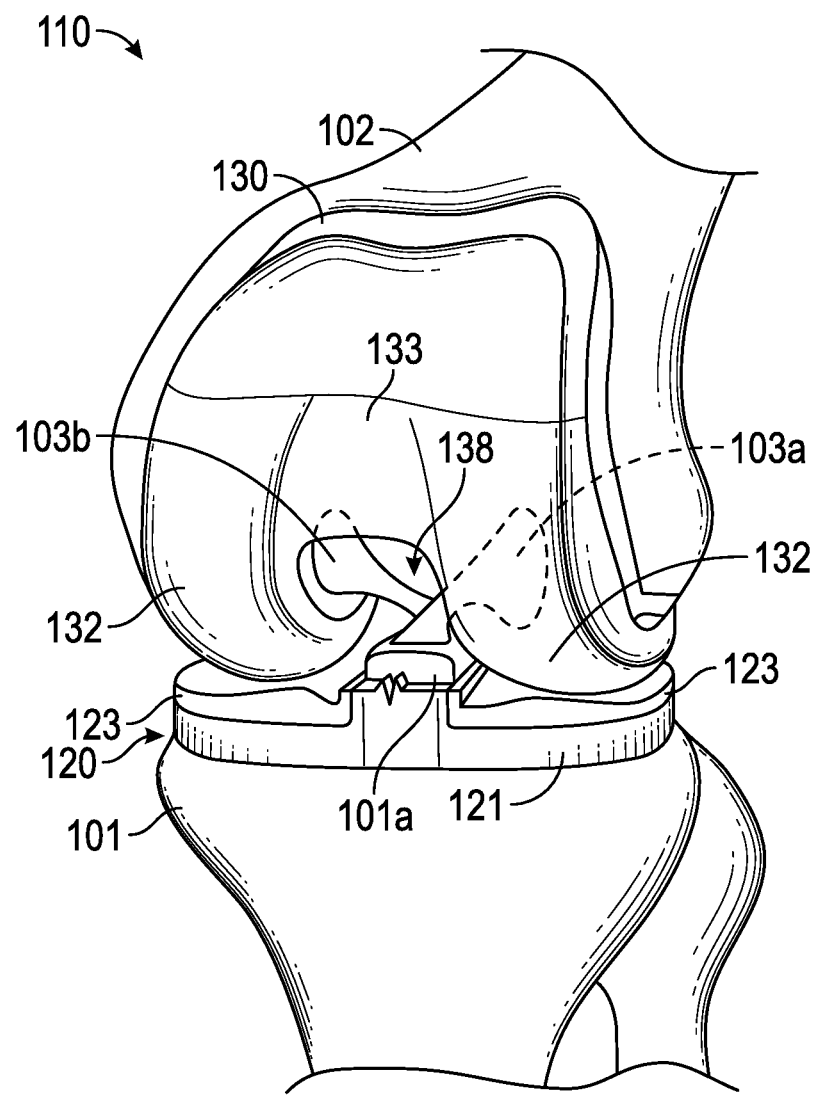
FIG. 1 illustrates a perspective view of a post-operative prosthetic knee joint fitted with a prosthetic system, consistent with an exemplary embodiment.

FIG. 1 illustrates a prosthetic implant system 110 implanted on a patient's knee. The prosthetic implant system 110 shown comprises a plurality of components, each of which is configured to replace a respective resected portion of the native knee joint. According to one embodiment, prosthetic implant system 110 may include a tibial implant system 120 and a femoral component 130. After installation during knee replacement surgery, tibial implant system 120 and femoral component 130 cooperate to replicate the form and function of a native knee joint.

Femoral component 130 may be secured to the distal end of femur 102 and configured to replace the structure and function of the native femoral portion of the knee joint 100. As such, femoral component 130 may be manufactured from surgical-grade metal or metal alloy material (such as surgical-grade steel, titanium, cobalt-chrome, etc.) that is substantially rigid for providing sufficient strength to support the forces required of the knee joint. According to one embodiment, femoral component 130 may embody a single component having a plurality of different structural features, each configured to perform a particular function associated with the knee joint. For example, femoral component 130 may comprise a pair of condyles 132, each of which is coupled to a patellar guide portion 133. The pair of condyles 132 may be separated from one another by an intercondylar notch 138, which provides a channel through which one or more cruciate ligaments 103, such as anterior cruciate ligament (ACL) 103a and/or posterior cruciate ligament (PCL) 103b, may pass.

Femoral component 130 may be configured to engage and articulate with portions of tibial implant system 120, as shown in FIG. 1. During use, the femur is rotated relative to the tibia during flexion and extension, which causes femoral component 130 depicted in FIG. 1 to rotate relative to a base portion 121 across the top surface of insert portions 123.

Figure 2A:
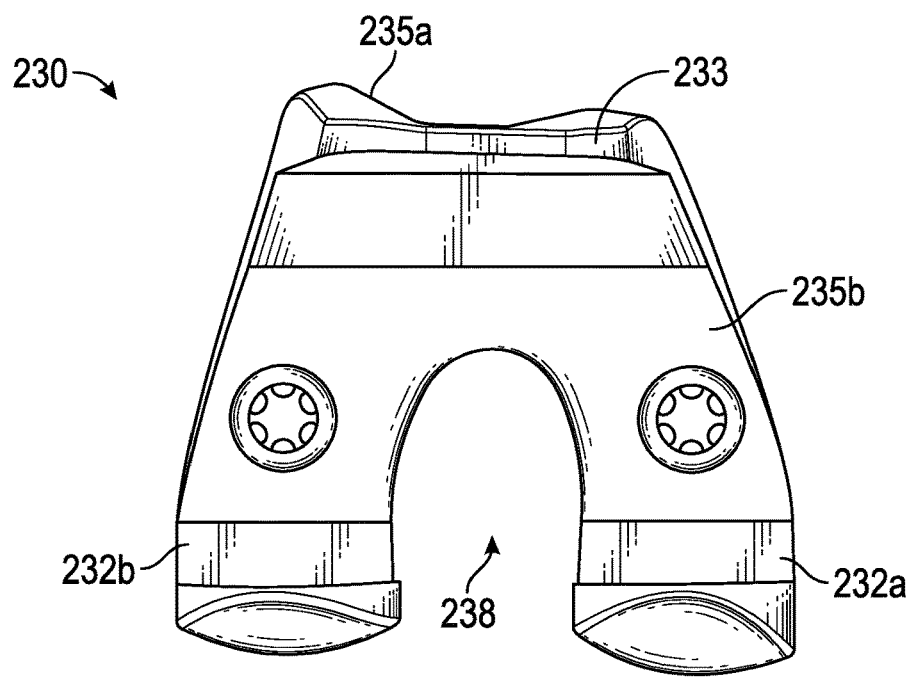
FIG. 2A illustrates a top view of a first exemplary embodiment of a prosthetic component.
Figure 2B:
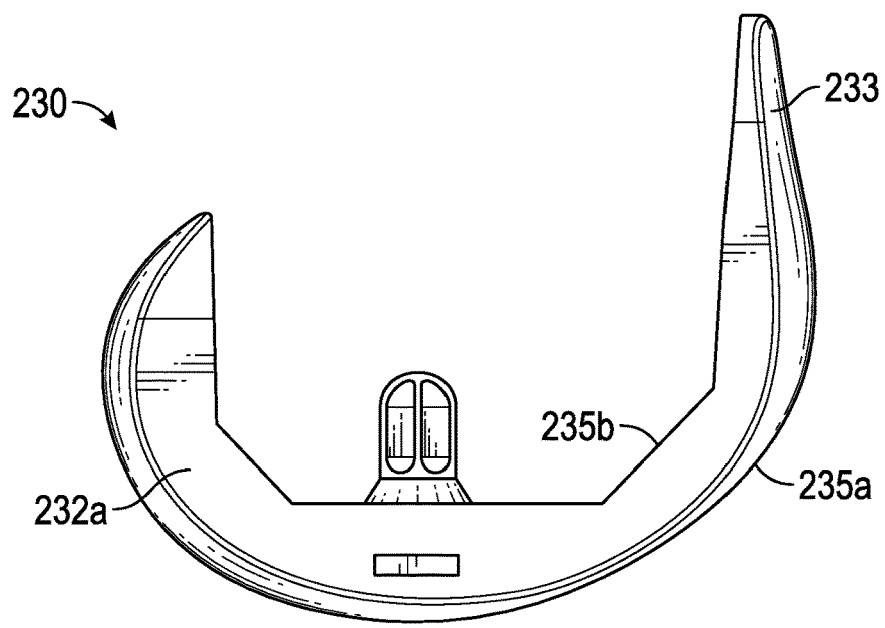
FIG. 2B illustrates a side view of the first exemplary embodiment of a prosthetic component.
Figure 2C:
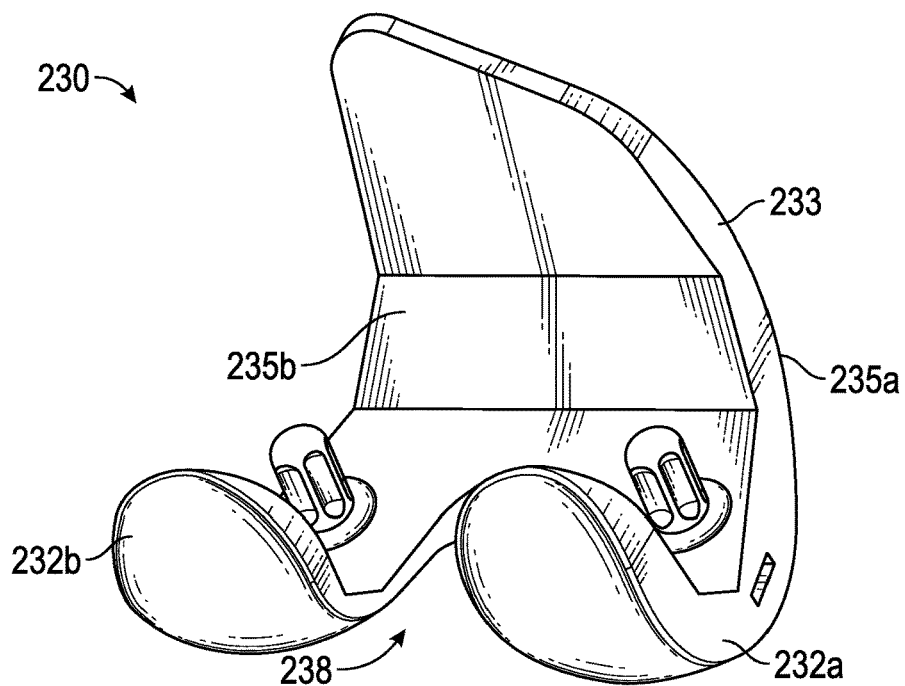
FIG. 2C illustrates a posterior perspective view of the first exemplary embodiment of a prosthetic component.

Referring particularly to FIGS. 2A-2C (and similarly shown in the embodiments of FIGS. 3A-26), the body portion of femoral component 230 comprises a patellar guide portion 233 and a pair of condyles 232, including a medial condyle 232a and lateral condyle 232b. Patellar guide portion 233 of femoral component 230 may extend from the front of the distal end of the femur and curve downward toward the intercondylar fossa of the femur, which is exposed by intercondylar notch 238. Medial and lateral condyles 232a, 232b project from the bottom of patellar guide portion 233 and extend on either side of intercondylar notch 238, around the underside of the femur and continuing toward the posterior of the femur.

The body portion of femoral component 230 also includes a bearing surface 235a and an interface surface 235b. Bearing surface 235a comprises a curved, outward-facing (inferior) surface formed by patellar guide portion 233 and condyles 232. Accordingly, bearing surface 235a is configured to articulate with one or more features of the knee joint, such as the patella (not shown). Interface surface 235b comprises the inner (superior) surface of femoral component 230 and is configured to engage with and attach to the resected surface of femur 102. The above-noted characteristics of femoral component 230 may be included, alone or in combination, as part of each of the exemplary embodiments discussed herein, though specific reference to these features in each embodiment may not be made.

According to the embodiment of FIGS. 2A-2C, interface surface 235b may include a plurality of planar surfaces, each of which corresponds to a resected plane of the femur that has been prepared using a cutting tool having a planar cutting blade. The planar surfaces of the interface surface 235b of femoral component 230 are configured to match with an anterior cut, an anterior chamfer cut, a distal cut, a posterior chamfer cut, and a posterior cut. Although illustrated as having five planar surfaces in the baseline embodiment of FIGS. 2A-2C, it is contemplated that interface surface 235b may be configured as having any shape suitable for engagement with a resected surface of the femur.

Indeed, with increasing use and capabilities of computer-assisted surgery (CAS) systems (such as that depicted in FIG. 28 and discussed below), a user may have the freedom to perform a greater variety of cuts, using a variety of tools to prepare the resected surface of the bone. Advantageously, with the ability to make these cuts more efficiently and with greater ease, prosthetic components, and interface surfaces in particular, may be configured in such a way that minimizes the amount of bone that must be resected to prepare the bone, such as the distal end of the femur, to receive the prosthetic component. Other advantages of enhanced interface surface designs include better fixation of the implant on the bone, thinner implants, shorter operating room time, and minimizing stresses and strains on the bone, implant, and fixation cement. Finally, enhanced component designs (made possible by the advances in CAS technology and systems) may allow for tailoring the component to patient-specific anatomy, which can similarly provide the advantages noted above and can result in greater longevity of the component. FIGS. 3A-12 show various exemplary embodiments exhibiting the component variations to minimize resected bone and provide at least the advantages described above.

Figure 3A:
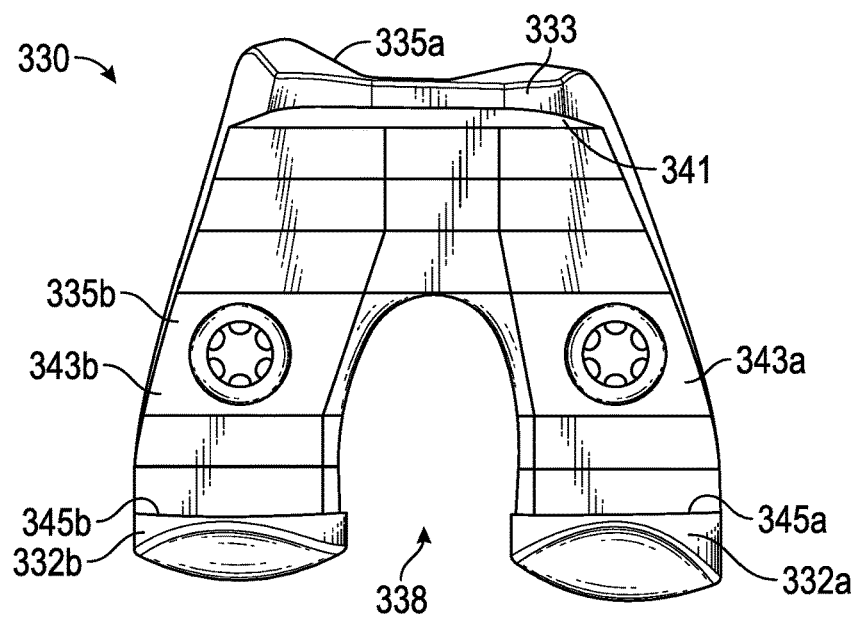
FIG. 3A illustrates a top view of a second exemplary embodiment of a prosthetic component.
Figure 3B:
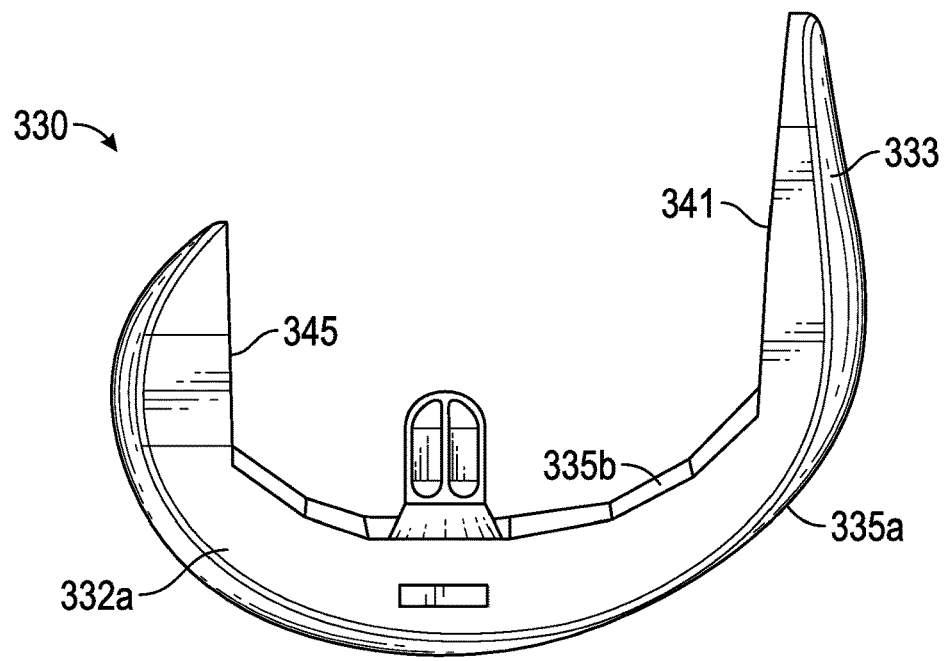
FIG. 3B illustrates a side view of the second exemplary embodiment of a prosthetic component.
Figure 3C:
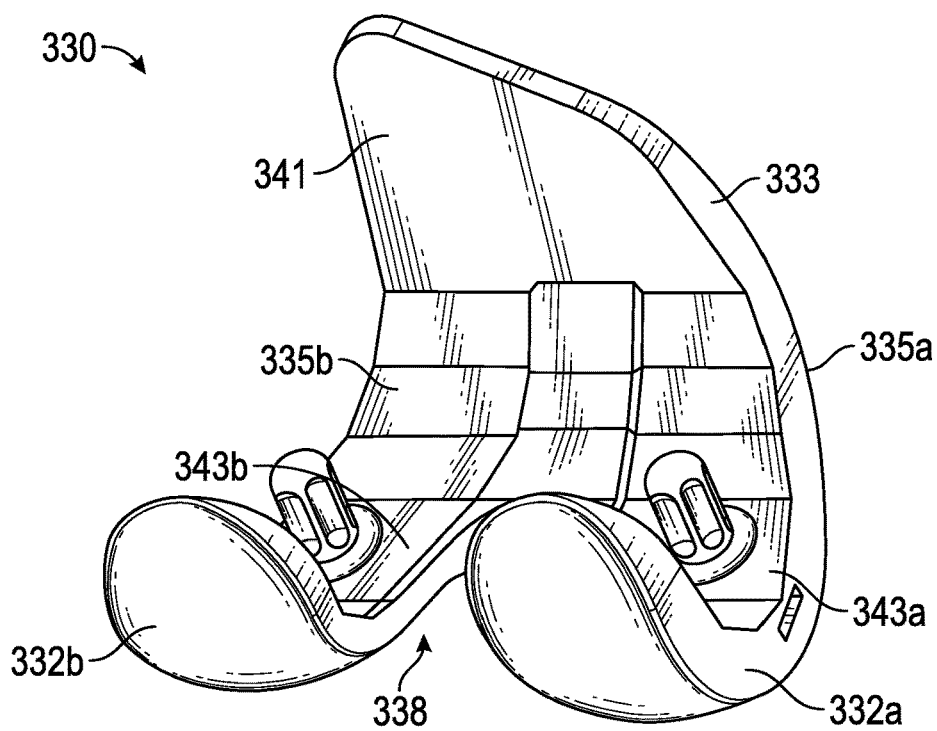
FIG. 3C illustrates a posterior perspective view of the second exemplary embodiment of a prosthetic component.

Referring to FIGS. 3A-3C, femoral component 330 has a multi-planar interface surface 335b. In the embodiment shown, the interface surface 335b has eight planar surfaces, though any number of planar surfaces may be used. The planar faces include, at least, an anterior face 341, distal face 343, and posterior face 345. Distal face 343 includes distal face portion 343a at least partially on medial condyle 332a and distal face portion 343b at least partially on lateral condyle 332b. Similarly, posterior face 345 includes posterior face portion 345a at least partially on medial condyle 332a and posterior face portion 345b at least partially on lateral condyle 332b. As the number of planar surfaces of the interface surface 335b increases, the more closely the interface surface 335b resembles a fully contoured surface between anterior face 341 and posterior face 345. Preparing a bone to receive a prosthetic component having a contoured interface surface 335b allows for the greatest amount of bone to be conserved. Conversely, larger straight cuts require a greater amount of bone to be resected. The embodiment of FIGS. 3A-3C, having several planar surfaces on its interface surface 335b, requires less bone removal than, for example, the embodiment shown in FIGS. 2A-2C. While nearly resembling a contoured interface surface 335b and thus providing improved bone conservation, the multi-planar configuration also allows for use of a single tool throughout the preparation process (such as a tool having a planar blade, i.e. straight cut sagittal saw), and is intended to reduce operating room time over configurations that may require changing between tools (for example, to a rotary cutting tool) during the procedure.

Figure 4A:
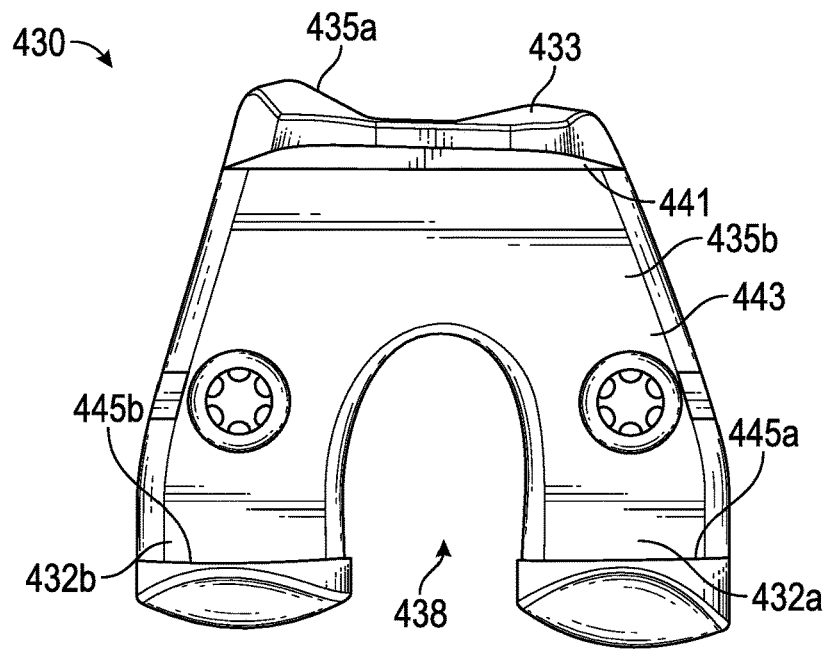
FIG. 4A illustrates a top view of a third exemplary embodiment of a prosthetic component.
Figure 4B:
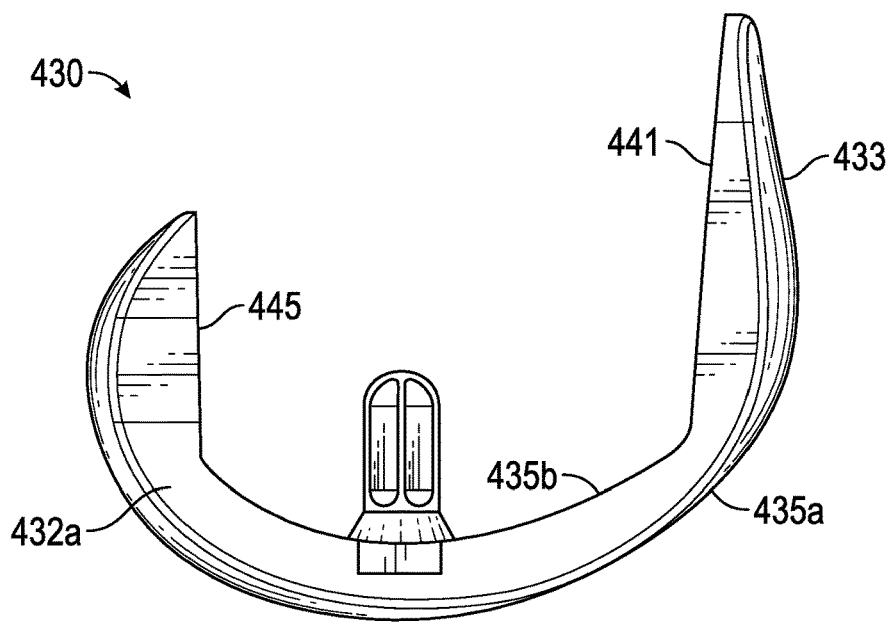
FIG. 4B illustrates a side view of the third exemplary embodiment of a prosthetic component.
Figure 4C:
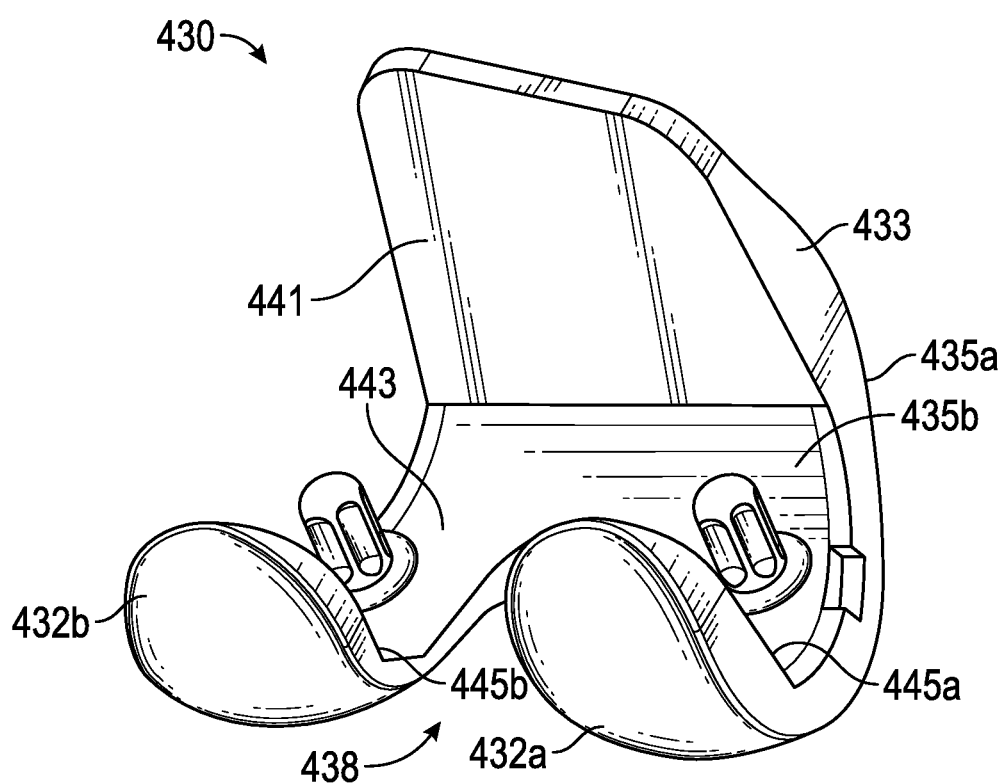
FIG. 4C illustrates a posterior perspective view of the third exemplary embodiment of a prosthetic component.

FIGS. 4A-4C depict an embodiment of a femoral component 430 having a fully contoured interface surface 435b between anterior face 441 and posterior face 445. A fully contoured configuration is a preferred configuration for maximum bone conservation. A prepared contoured surface of the distal femur 102, made possible by using a rotary cutting tool, such as a burr, rather than a sagittal saw for at least some cuts, requires the removal of less bone from the femur 102. A fully contoured interface surface 435b can also advantageously produce a relatively thin implant compared with the profile of the embodiments of FIGS. 2A-2C and 3A-3C.

Figure 5A:
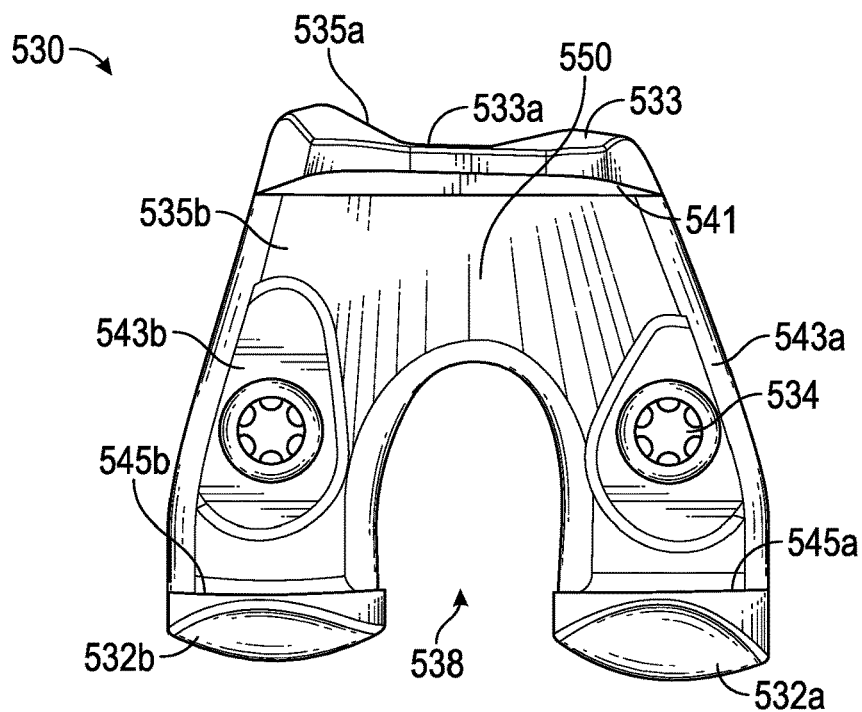
FIG. 5A illustrates a top view of a fourth exemplary embodiment of a prosthetic component.
Figure 5B:
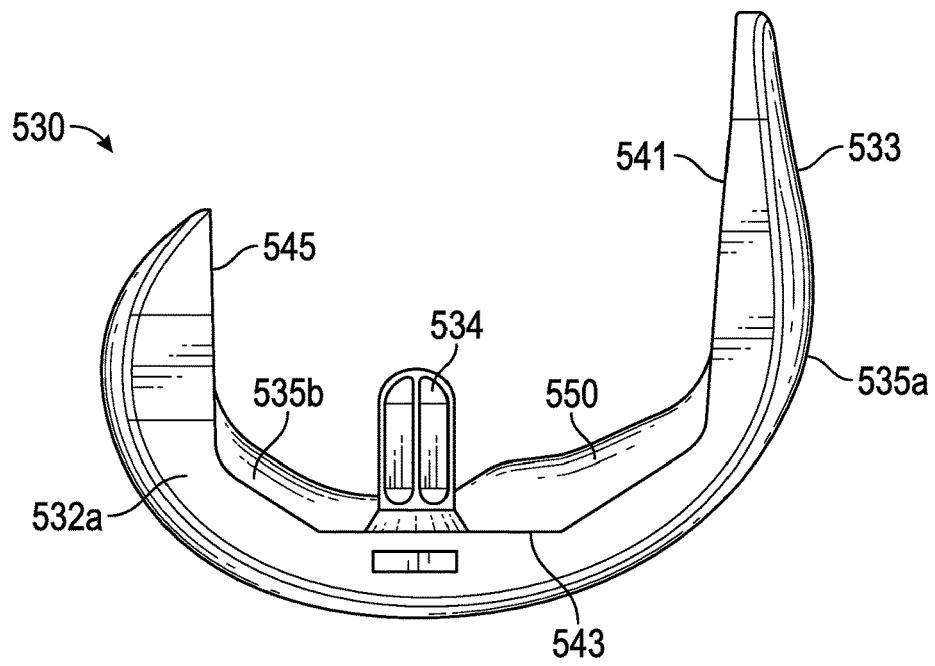
FIG. 5B illustrates a side view of the fourth exemplary embodiment of a prosthetic component.
Figure 5C:
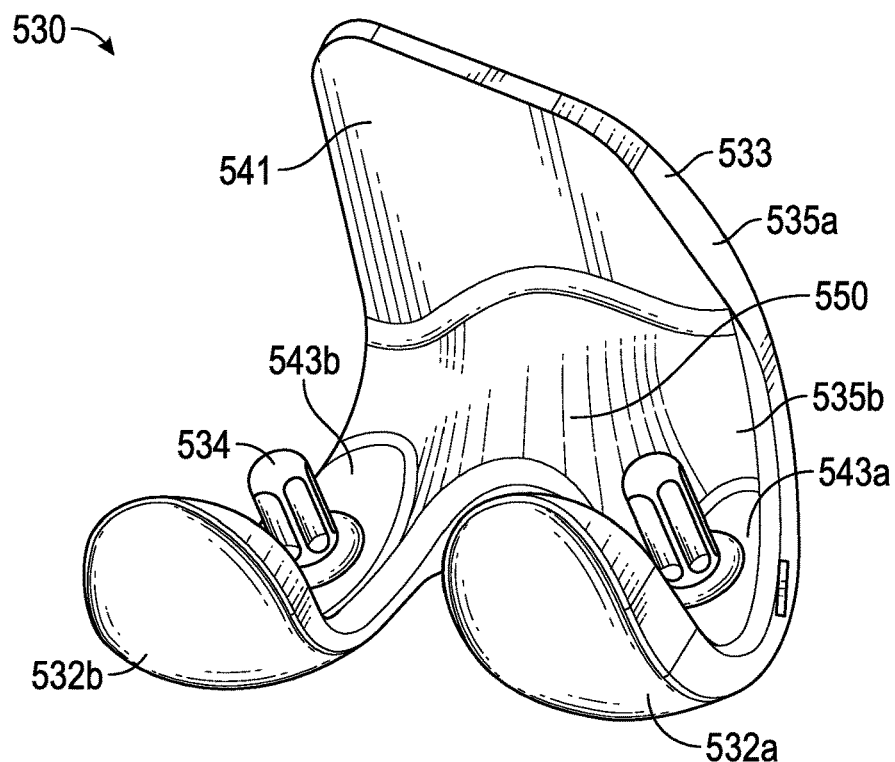
FIG. 5C illustrates a posterior perspective view of the fourth exemplary embodiment of a prosthetic component.

FIGS. 5A-5C depict a femoral component 530 having an interface surface 535b with a hybrid configuration. Femoral component 530 has an anterior face 541 and posterior face 545 separated by a contoured surface with a distal flat portion 543, having a first distal flat 543a and a second distal flat 543b. The configuration of the interface surface 535b is a preferred embodiment for its bone conservation advantages (by way of the substantially curved surface between anterior face 541 and posterior face 545), but as an advantage over the fully contoured configuration of FIGS. 4A-4C, the hybrid configuration of femoral component 530 may also be preferred by surgeons accustomed to flat planar surfaces to aide in positioning and orientation with confidence. Bone preparation to receive femoral component 530 utilizes both a rotary cutter and a straight cut sagittal saw to shape the bone to match interface surface 535b. Other features of the embodiment of FIGS. 5A-5C, such as the median groove 533a, canopy 550, and elongated projections 534 will be discussed in greater detail below.

Figure 6:
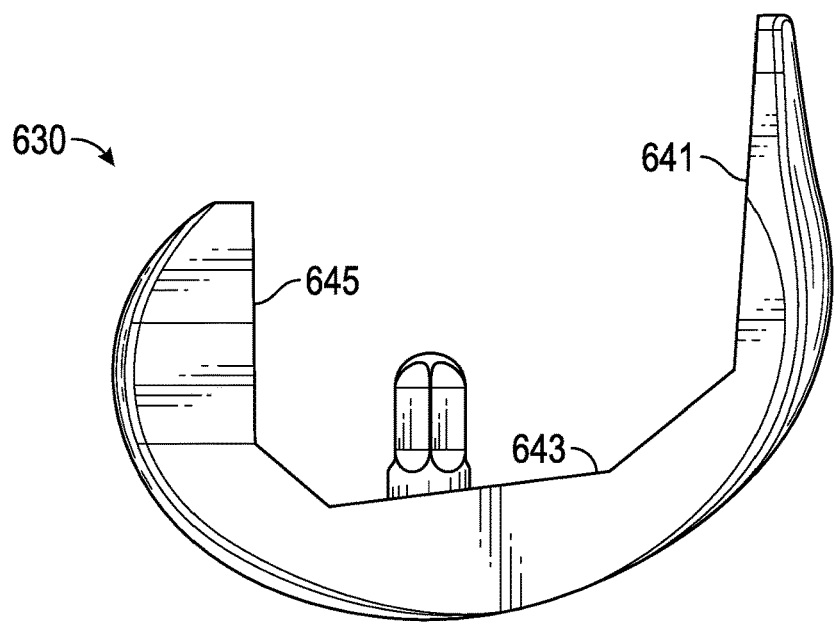
FIG. 6 illustrates a side view of a fifth exemplary embodiment of a prosthetic component.
Figure 7:
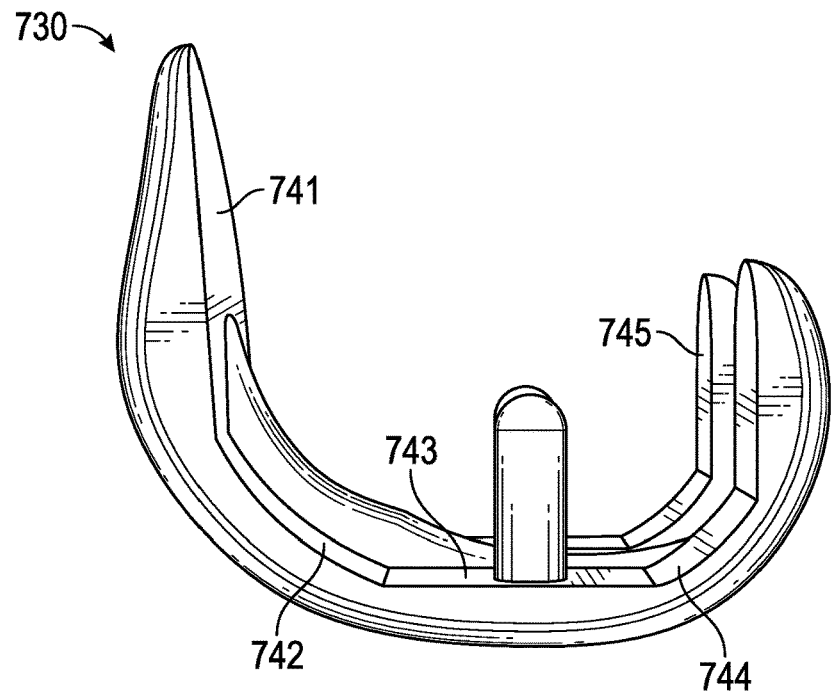
FIG. 7 illustrates a side view of a sixth exemplary embodiment of a prosthetic component.
Figure 8:
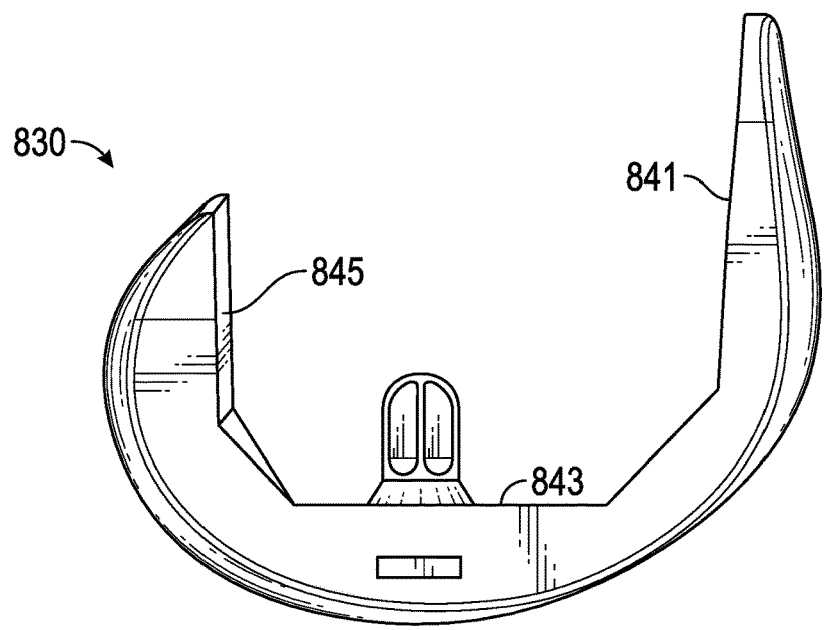
FIG. 8 illustrates a side perspective view of a seventh exemplary embodiment of a prosthetic component.

Other exemplary femoral components are shown in FIGS. 6-8. These exemplary embodiments depict various ways in which femoral components, particularly the interface surface of femoral components, can be modified in order for bone conservation, better patient-specific fit, thinner implant profile, and other component enhancements. As shown in FIG. 6, femoral component 630 has an anterior face 641, distal face 643, and posterior face 645. In the embodiment shown, distal face is angled distally from anterior face 641 towards posterior face 645. Femoral component 730 shown in FIG. 7 also includes an anterior face 741, distal face 743, and posterior face 745. In this embodiment, between each of the planar cut segments at the faces 741, 743, and 745 is a non-planar surface segment such as cylindrical chamfer cuts 742 and 744. Cylindrical chamfer cuts 742, 744 provide a smooth, curved transition between the faces 741, 743, 745 of interface surface 735b, which as noted above, lessens the amount of bone that must be removed to prepare the bone to receive the implant. Any combination of planar segments and non-planar surface segments may be used in an embodiment similar to provide a substantially contoured interface surface between anterior face 741 and posterior face 745. In the exemplary embodiment of FIG. 8, femoral component 830 also comprises an anterior face 841, distal face 843, and posterior face 845. In this embodiment, posterior face 845 is pitched. This pitched surface more closely matches the anatomic configuration of the femur 102, therefore requiring less bone removal while still maintaining a substantially uniform thickness of the component 830 from the bone.

Figure 9A:
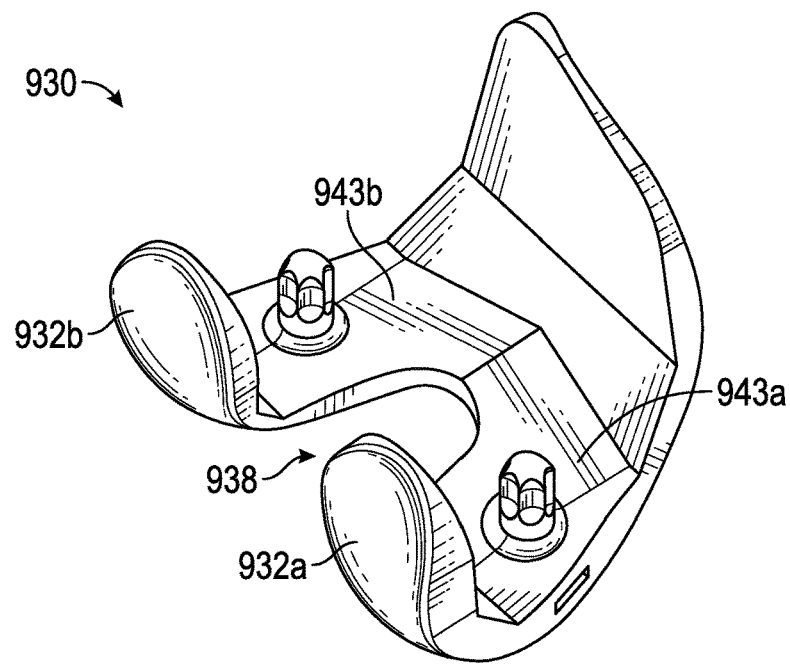
FIG. 9A illustrates a perspective view of an eighth exemplary embodiment of a prosthetic component.
Figure 9B:
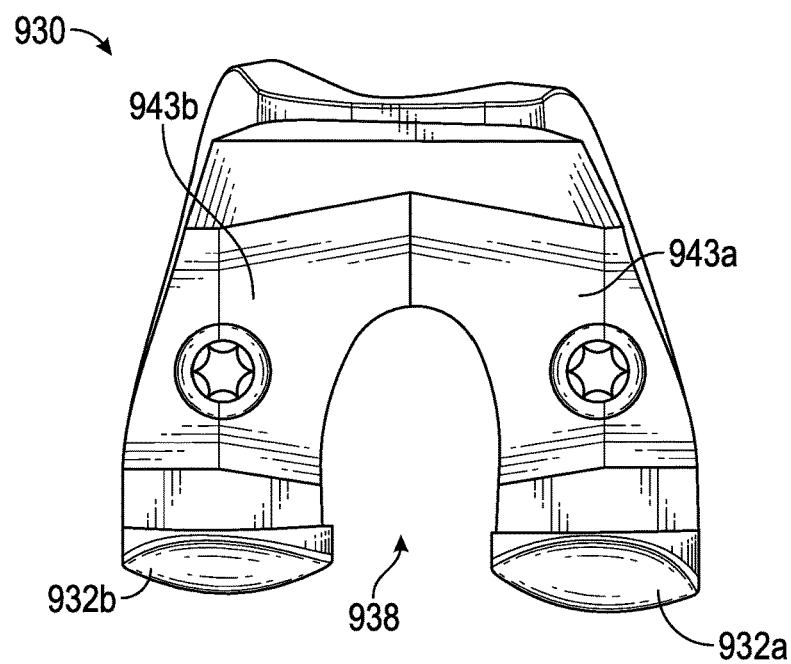
FIG. 9B illustrates a top view of the eighth exemplary embodiment of a prosthetic component.
Figure 10A:
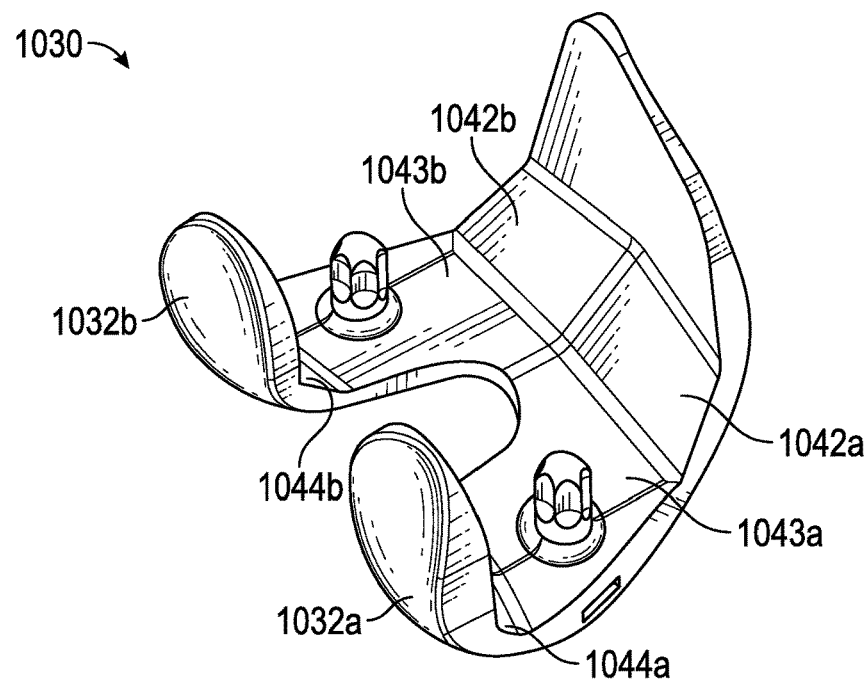
FIG. 10A illustrates a perspective view of a ninth exemplary embodiment of a prosthetic component.
Figure 10B:
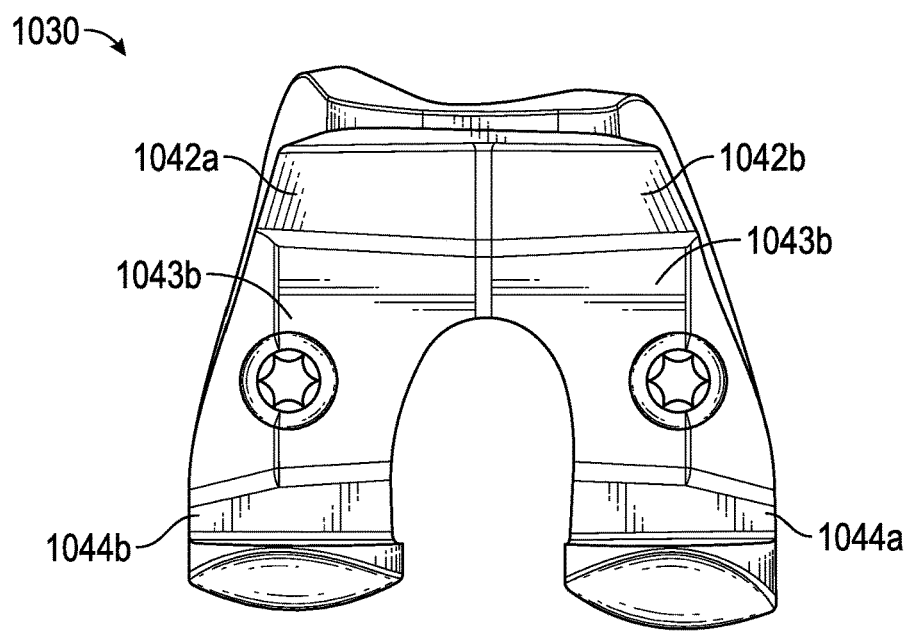
FIG. 10B illustrates a top view of the ninth exemplary embodiment of a prosthetic component.
Figure 11A:
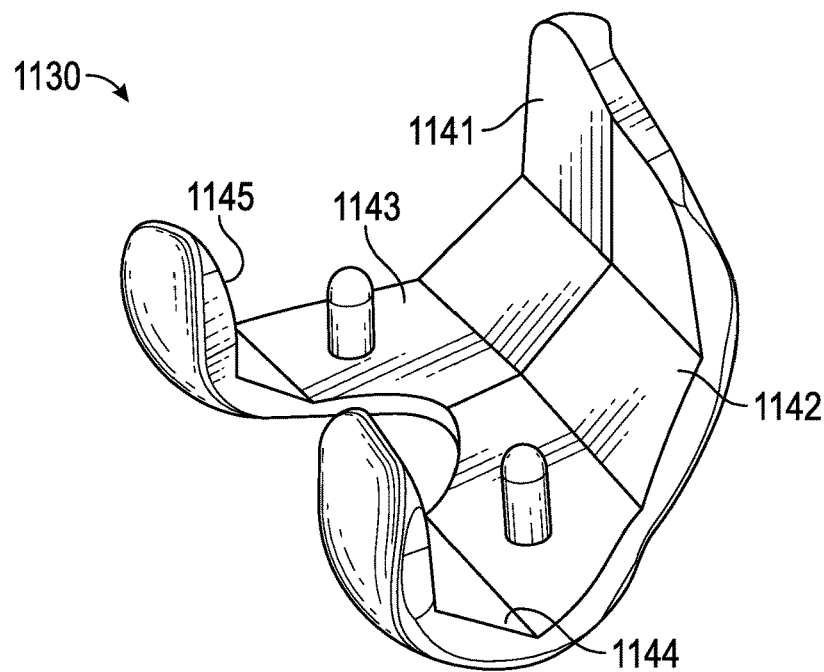
FIG. 11A illustrates a perspective view of a tenth exemplary embodiment of a prosthetic component.
Figure 11B:
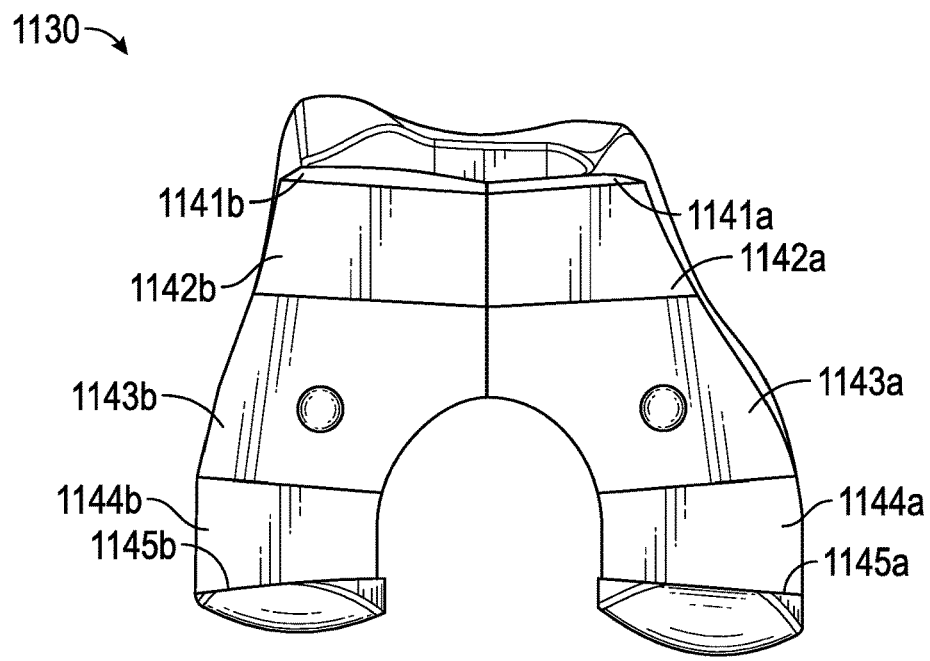
FIG. 11B illustrates a top view of the tenth exemplary embodiment of a prosthetic component.

Other embodiments for conserving bone during resection and preparation to receive a femoral component include pitched planar surfaces on the interface surfaces. The embodiments of FIGS. 9-11 depict variations of the five-cut femoral component 230 of FIGS. 2A-2C. FIGS. 9A-9B show femoral component 930 having a pitched distal surface 943. As shown, two pitched planes 943a and 943b converge towards the center axis (extending substantially along intercondylar notch 938 and between condyles 932) of femoral component 930 to create the pitched distal surface 943. The embodiment of FIGS. 10A-10B depicts femoral component 1030 having a pitched distal surface 1043, as well as a pitched anterior chamfer 1042 and posterior chamfer 1044. Femoral component 1130, shown in FIGS. 11A-11B, includes all five pitched surfaces on interface surface 1135b, including pitched anterior face 1141, anterior chamfer 1142, distal face 1143, posterior chamfer 1144, and posterior face 1145.

Figure 12A:
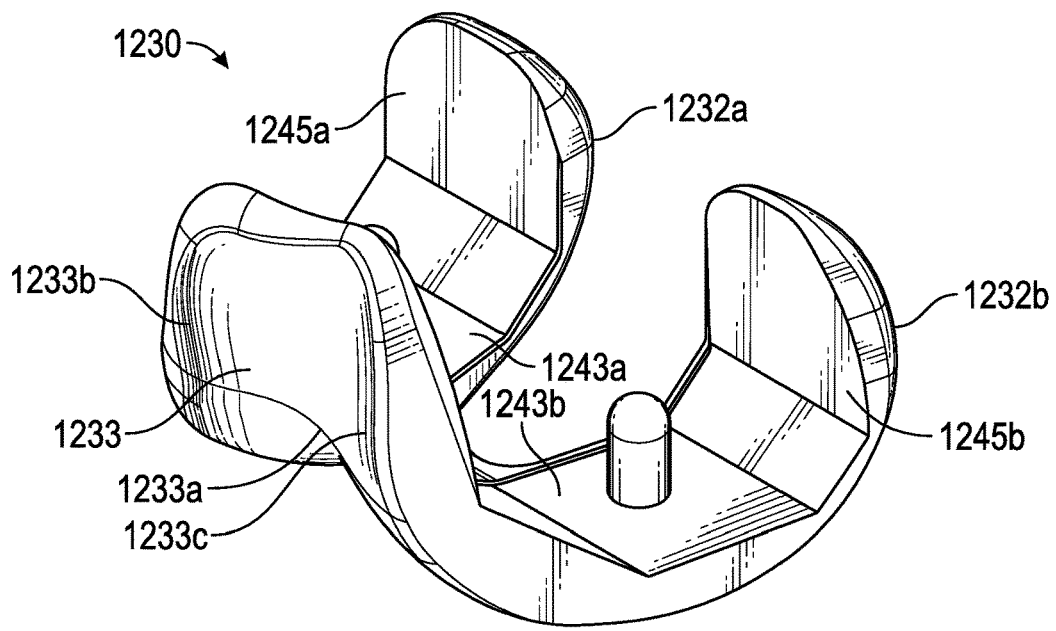
FIG. 12A illustrates a front perspective view of an eleventh exemplary embodiment of a prosthetic component.
Figure 12B:
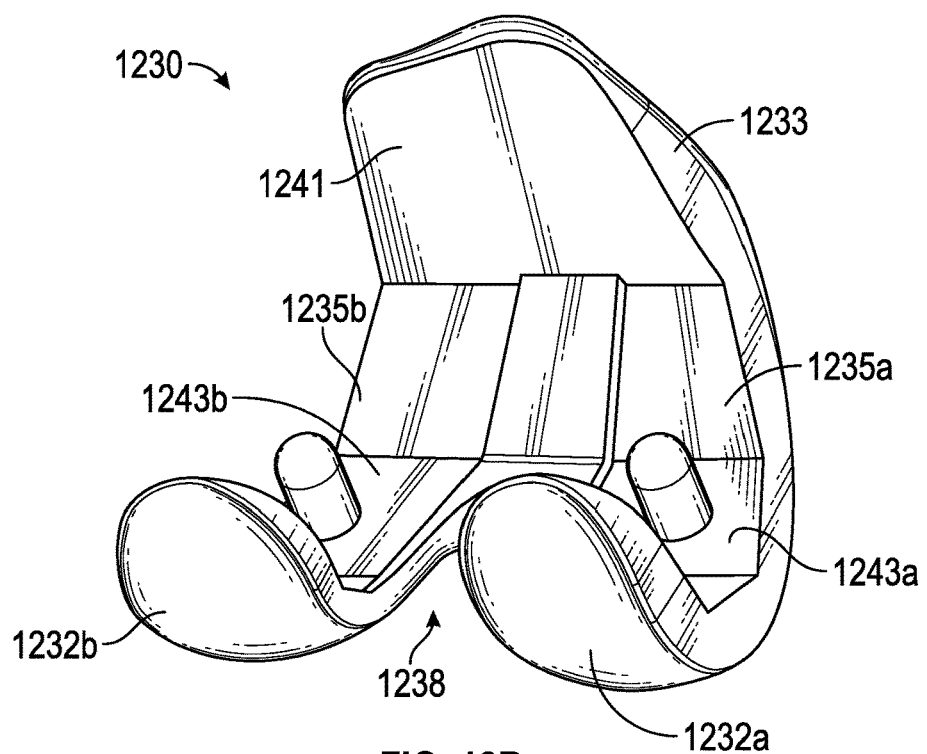
FIG. 12B illustrates a rear perspective view of the eleventh exemplary embodiment of a prosthetic component.
Figure 13A:
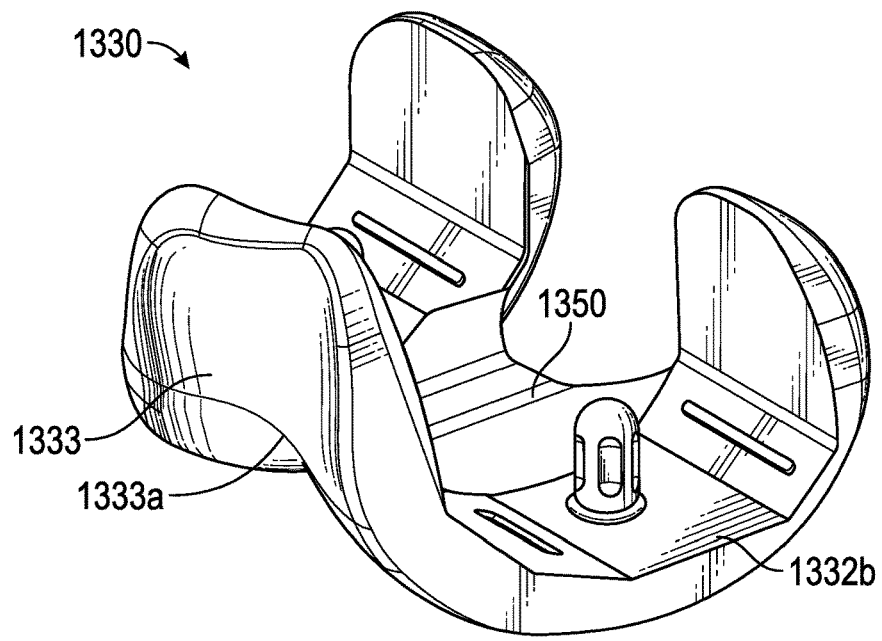
FIG. 13A illustrates a front perspective view of a twelfth exemplary embodiment of a prosthetic component.
Figure 13B:
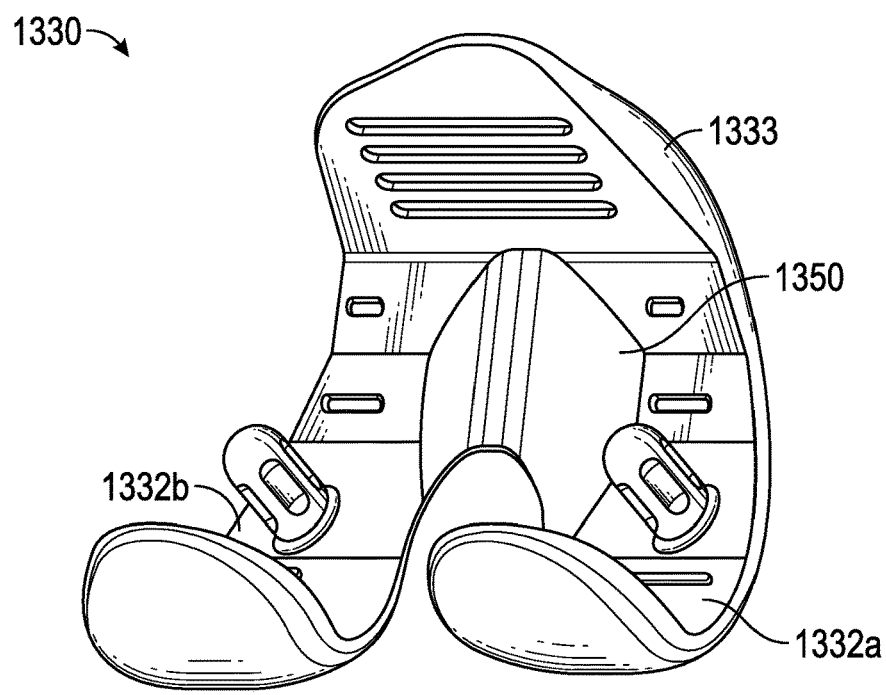
FIG. 13B illustrates a rear perspective view of the twelfth exemplary embodiment of a prosthetic component.
Figure 14A:
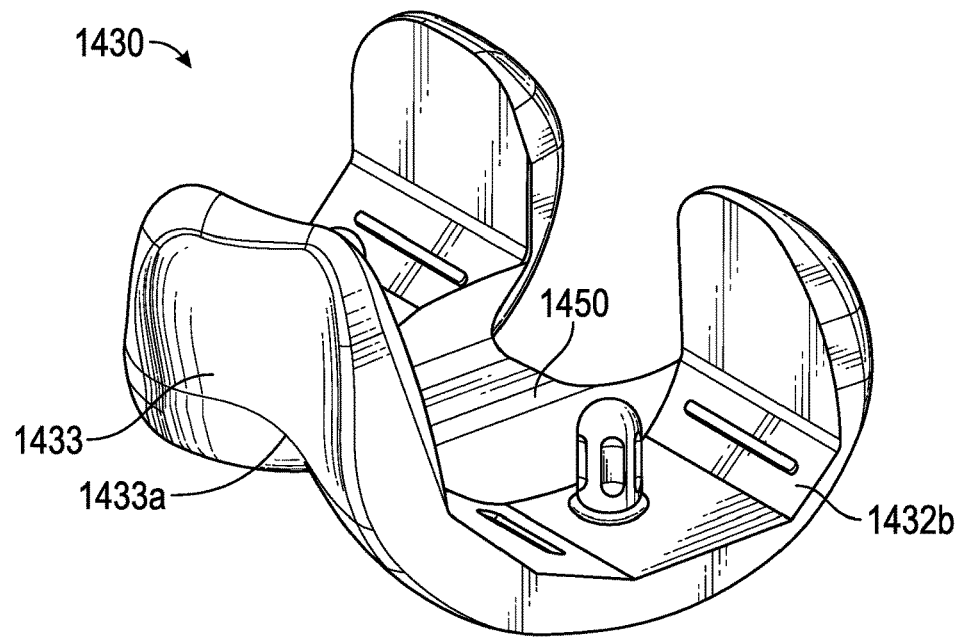
FIG. 14A illustrates a front perspective view of a thirteenth exemplary embodiment of a prosthetic component.
Figure 14B:
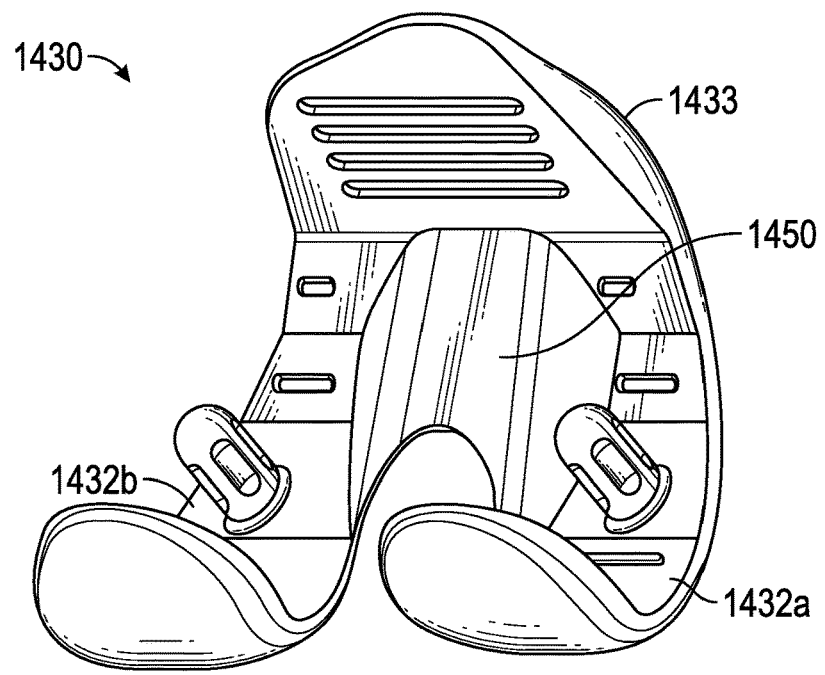
FIG. 14B illustrates a rear perspective view of the thirteenth exemplary embodiment of a prosthetic component.

The patellar guide portion of femoral components, such as patellar guide portions 1233, 1333 and 1433 of FIGS. 12-14, may be configured to emulate the structure and function of the native patellar surface, which is located on the front of the distal end of femur 102. For example, as shown in FIG. 12A, patellar guide portion 1233 includes a median groove 1233a that is located toward the center of patellar guide portion 1233. Located on either side of median groove 1233a and directly above respective condyles 1232a, 1232b are a plurality of raised surfaces 1233b, 1233c. Median groove 1233a provides the surface that articulates with the patella (or "kneecap," not shown), while raised surfaces 1233b, 1233c prevent the patella from sliding outside of median groove 1233a. Similarly, FIGS. 13A and 14A portray median groove 1333a and 1433a, respectively.

In accordance with the present embodiments, one feature of enhanced femoral component structures may be femoral components having a thinner profile, to improve bone conservation, overall effectiveness, and patient satisfaction in the implanted component. In order to accommodate both the thinner profile and a deep median groove (1233a, 1333a, or 1433a, for example) to emulate the structure and function of the native patellar surface, the interface surface of the femoral component may include a raised canopy portion, such as canopy 1250, 1350, 1450. The raised canopy provides for the median groove on the bearing surface (such as bearing surfaces 1235a, 1335a, and 1435a) without requiring the patellar guide portion and portions of the medial and lateral condyles to take on a thickness that accommodates the depth of the groove.

The raised canopy can take on a variety of shapes and configurations. As shown in FIG. 12B, canopy 1250 has a boxed configuration. In the embodiment of FIG. 13B, canopy 1350 takes on a v-shaped configuration. And in the embodiment shown in FIG. 14B, canopy 1450 has an arched configuration. The various configurations of the canopies may utilize various bone preparation methods and tools. The bone preparation for the boxed configuration of FIG. 12B may include a straight saw cut and two reciprocal cuts. The bone preparation for the v-shaped configuration of FIG. 13B may include two saw cuts in a "v" formation. The bone preparation for the arched configuration of FIG. 14B may include a cut or cuts using a reamer. The surgical system depicted in FIGS. 28-29 may be used to plan bone preparation and to perform the bone preparation cuts.

Figure 15:
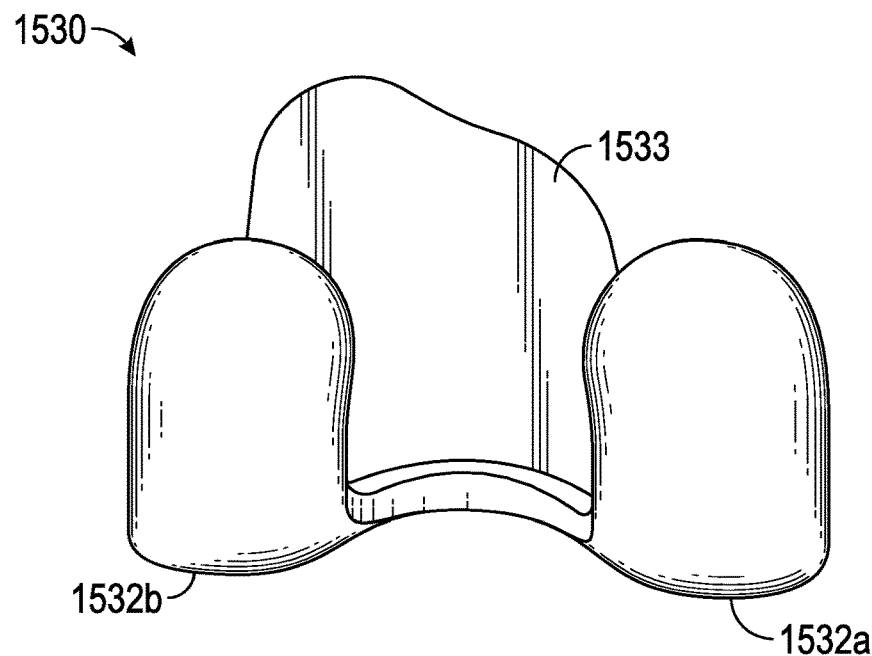
FIG. 15 illustrates a rear view of a fourteenth exemplary embodiment of a prosthetic component.

As discussed above with reference to FIGS. 1-2, and now particularly referring to FIG. 15, condyles 1532 may comprise medial condyle 1532a and lateral condyle 1532b. Condyles 1532 are configured to replace the structure and function of the corresponding native condyles of the femur. As such, condyles 1532 project from the lower portion of patellar guide portion 1533 on the anterior side of femur 102, curve around the underside of femur 102, and extend to the posterior side of femur 102. Condyles 1532 are configured to provide the primary structural and articular support for the femoral component of the knee joint. In an exemplary embodiment depicted in FIG. 15, the posterior portion of condyles 1532 are curved inwardly towards a center axis of the component 1530 (extending substantially along intercondylar notch 1538 and between condyles 1532) to more closely match the anatomic shape of the posterior region of the femur 102. Condyles 1532 having a curved posterior shape may allow for a more natural feel for the patient during the range of motion from flexion to extension. The configuration may also provide better contact with the tibia or a tibial component.

Figure 16:
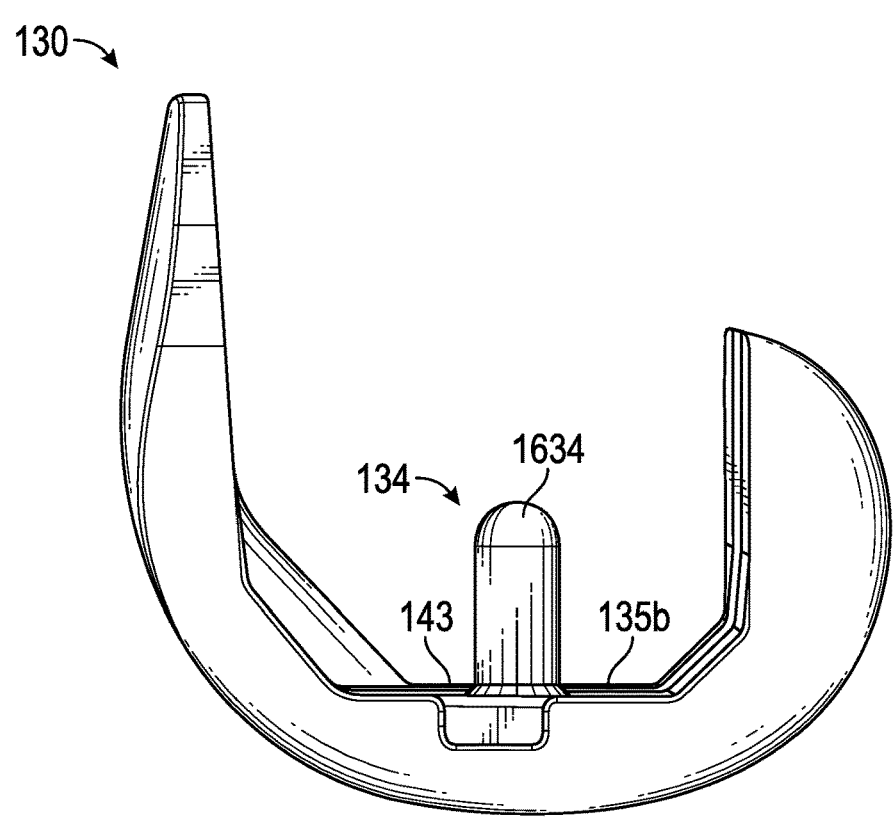
FIG. 16 illustrates a side view of a prosthetic component according to an exemplary embodiment having a first embodiment of an elongated projection.
Figure 17:
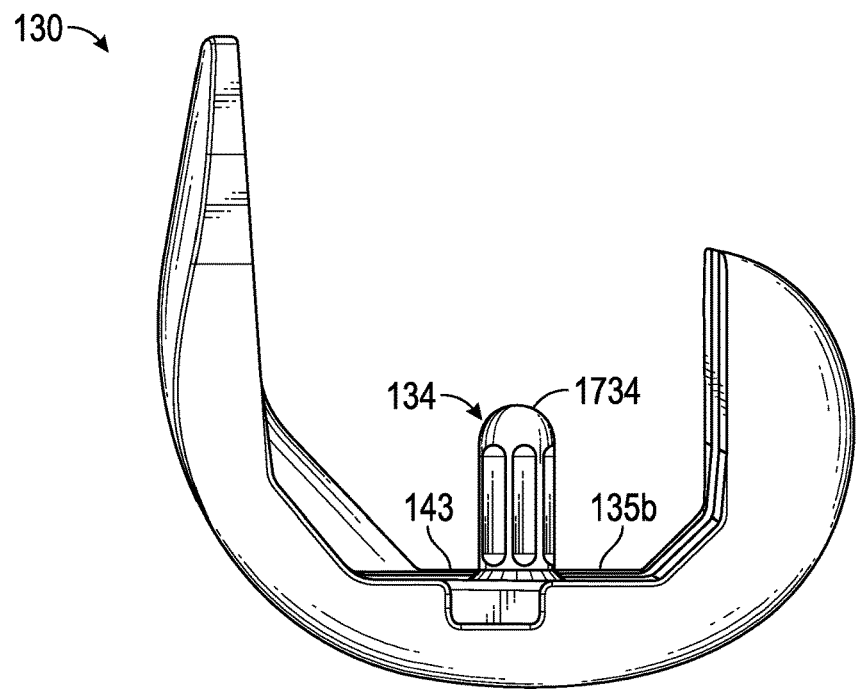
FIG. 17 illustrates a side view of a prosthetic component according to an exemplary embodiment having a second embodiment of an elongated projection.
Figure 18:
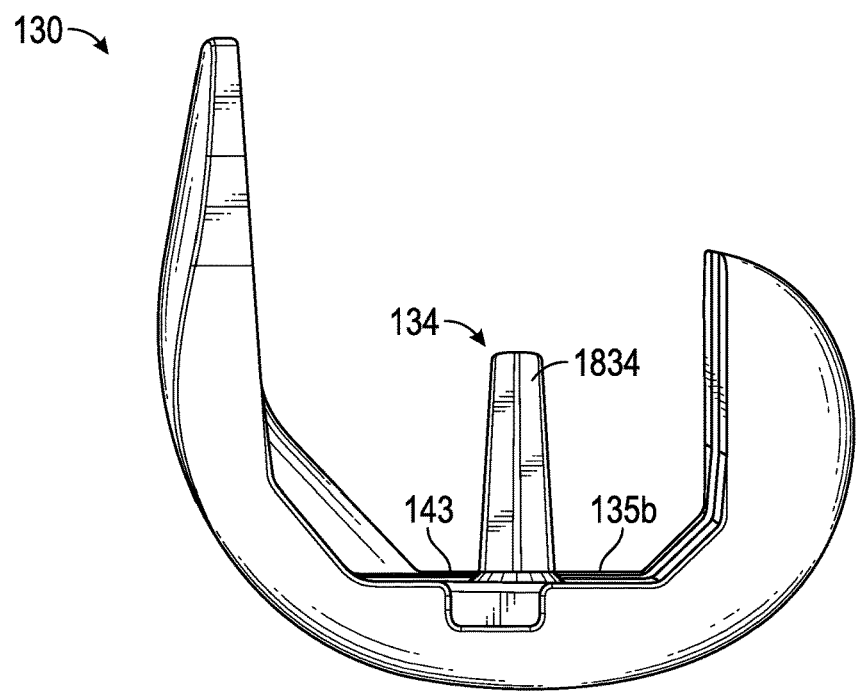
FIG. 18 illustrates a side view of a prosthetic component according to an exemplary embodiment having a third embodiment of an elongated projection.
Figure 25A:
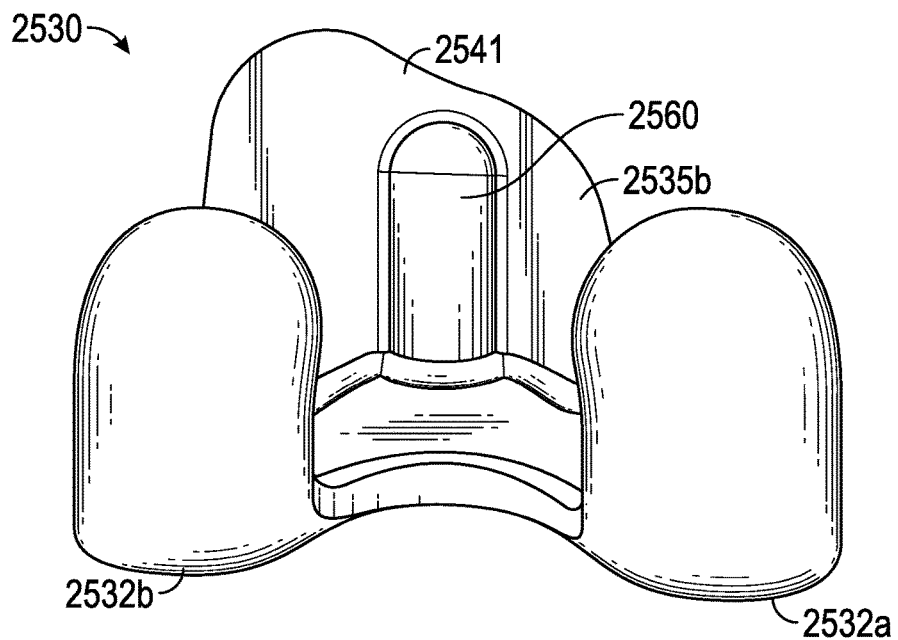
FIG. 25A illustrates a rear view of a fifteenth exemplary embodiment of a prosthetic component.
Figure 25B:
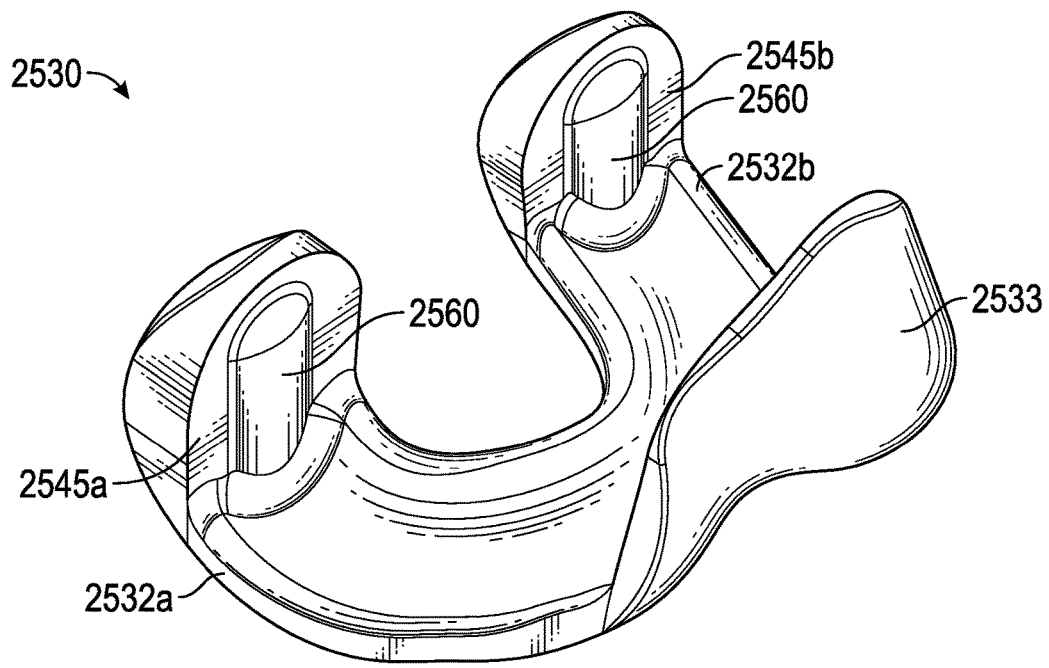
FIG. 25B illustrates a front perspective view of the fifteenth exemplary embodiment of a prosthetic component.
Figure 25C:
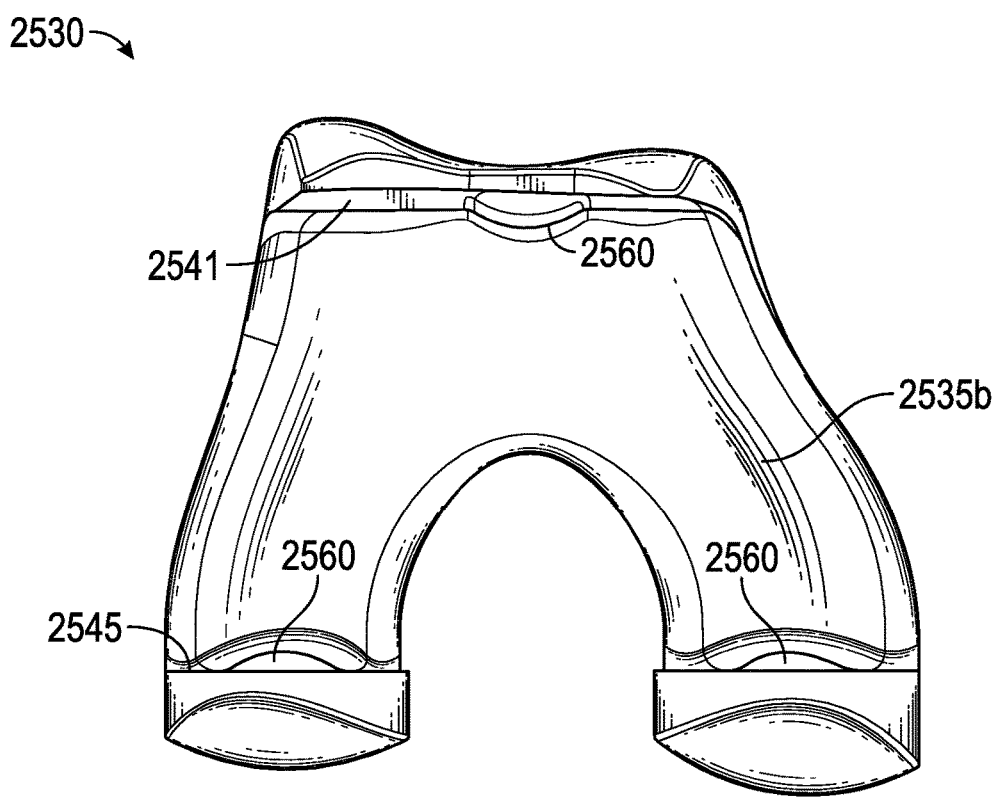
FIG. 25C illustrates a top view of the fifteenth exemplary embodiment of a prosthetic component.

As shown in FIGS. 16-18, femoral component 530 may include one or more elongated projections 134 that protrude from the interface surface 535b. Though the elongated projections 134 are depicted on femoral component 530, the elongated projections 134 discussed in this section may be used in combination with any of the femoral components discussed above. In preferred embodiments, elongated projections 134 are centered between the medial and lateral edges of each condyle 532a and 532b. Elongated projections 134 are also preferably centered anterior-posteriorly on the distal face 543.

Elongated projections 134 may be inserted into corresponding holes that have been surgically formed within femur 102 during a TKA procedure. The elongated projections 134 may be secured within the holes and configured to limit movement between femoral component 530 and femur 102. In an exemplary embodiment, elongated projections 134 are configured to be press fit into holes in the femur 102. Bone cement may be used to further secure the elongated projections 134 in the holes in the femur 102. The elongated projections 134 provide increased cement bonding surface area, and also provide stability while bonding cement is curing between other surfaces of the femur 102 and the femoral component.

FIGS. 16-18 depict various design combinations for the elongated projections 134. Elongated projections 134 may take on various forms, including by way of example, a cylinder (as in elongated projections 1634, 1734), a tapered cone (as in elongated projection 1834), a cruciform, or a dog bone configuration. The elongated projections 134 may have a smooth (as in elongated projection 1634) or textured finish (as in elongated projections 1734, 1834), such as blasted or fluted finish. Thin edges, such as those shown in FIGS. 17 and 18 may bite into the bone more readily than dull edges or more rounded configurations, and therefore can provide greater stability in a press fit engagement with the bone. At the same time, edges are preferably designed so as to not create micro-fractures in the bone as it is advanced into the hole formed in the bone. Finally, the elongated projections 134 may have varying tip designs, including by way of example a flat tip (as in elongated projection 1834), a tapered tip, or a round tip (as in elongated projections 1634, 1734). Though exemplary embodiments are shown in FIGS. 16-18, any combination of various forms, finishes, and tips may be used. It is contemplated that the embodiments and features of elongated projections 134 may also apply to projections for stabilizing other types of prosthetic components to bone, such as for stabilizing tibial components to the proximal tibia.

FIGS. 19-24 depict various embodiments of elongated projections that may be used with trial femoral components for confirming the size, geometry, position, and/or orientation of the selected femoral component. The trial projections 136 are preferably shorter than the elongated projections 134 so as not to disrupt the entire length of the holes in the bone, such that elongated projections on femoral component 530 can still achieve a press fit engagement when inserted. The trial projections 136 may have the same or different cross-sectional shape as the intended elongated projections 134. FIGS. 19-20 depict embodiments wherein the trial projection 136 has the same cross-sectional configuration as the elongated projection 134. FIGS. 19A-19B show an embodiment having a single slot therein, while FIGS. 20A-20B depict an embodiment that is t-slotted. The slots in the trial projections 136 allow for flexing of the projections as passed into the hole in the bone. FIGS. 21-22 depict embodiments having the same cross-sectional configuration as the elongated projection 134, but are intended to be shifted in orientation. In this way, small amounts of bone are engaged by the trial projections 136, but not at the same location as the intended elongated projection 134, thereby allowing the elongated projection 134 to also engage the bone. FIGS. 22A-22B depict an embodiment that is slotted. FIGS. 23-24 depict embodiments having a different cross-sectional shape as the intended elongated projections 134. In these figures, trial projections 136 have a triangle shape. In the embodiments shown, the edges of the triangle are configured to match up with the edges of elongated projections 134. As shown in the embodiments of FIGS. 19-24, the tip of the trial projections 136 may also vary, and may include flat, rounded, or tapered tip configurations.

In some embodiments, the femoral components may utilize alternative mechanisms to assist with fixation of the component to the bone. One such embodiment, such as femoral component 2530 shown in FIGS. 25A-25C, does not utilize elongated projections, but rather includes one or more half peg extensions 2560. Half pegs 2560 may be formed in the interface surface 2535*b* and are configured to fit into similarly shaped recesses in the prepared femur. In the embodiment shown, half pegs 2560 extend longitudinally along the anterior face 2541 and the posterior face 2445 on each of the condyles 2532. It is contemplated that half pegs 2560 may extend laterally along the anterior face 2541 and the posterior face 2545 on each of the condyles 2532, or may also be positioned on any portion of the interface surface 2535*b* between the anterior face 2541 and the posterior face 2545.

Figure 26A:
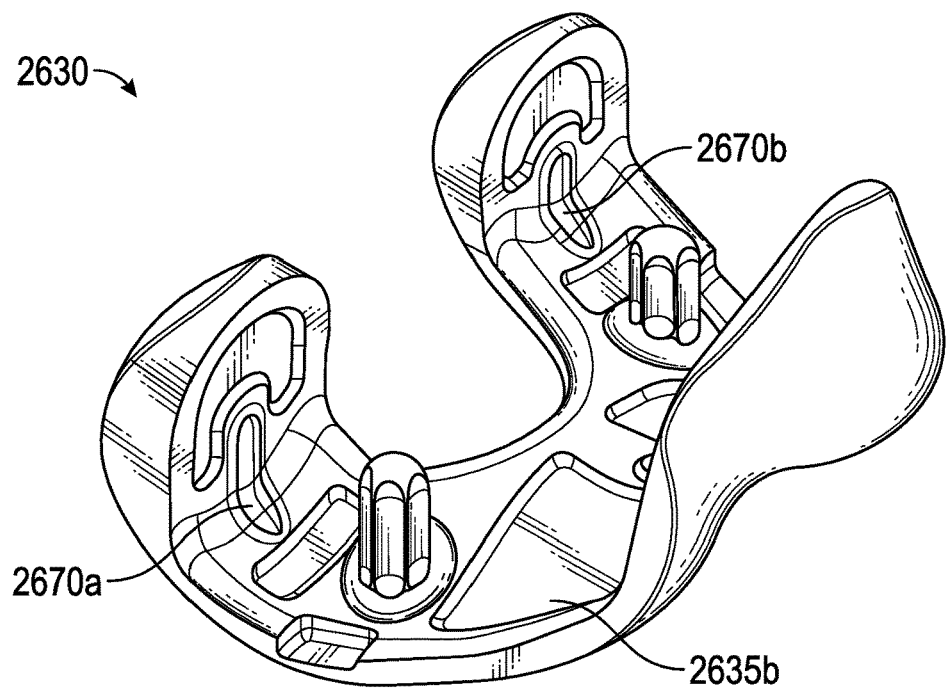
FIG. 26A illustrates a front perspective view of a sixteenth exemplary embodiment of a prosthetic component.
Figure 26B:
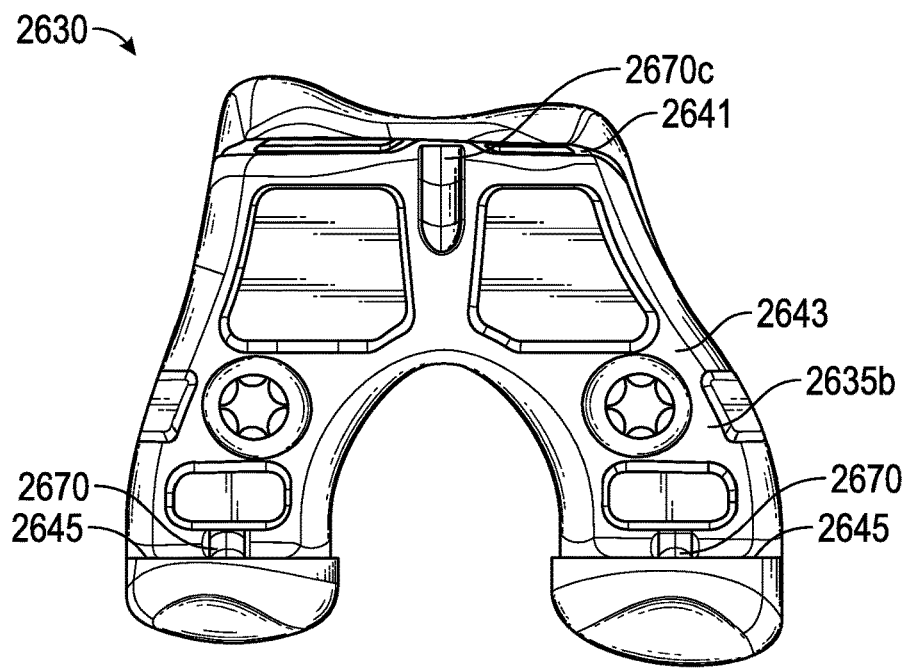
FIG. 26B illustrates a top view of the sixteenth exemplary embodiment of a prosthetic component.

FIGS. 26A-26B depict a femoral component 2630 utilizing both elongated projections 2634 and reinforcing keels 2670 formed in the interface surface 2635*b* to assist with fixation of the femoral component 2630 to the bone. In the embodiment shown, reinforcing keels 2670*a* and 2670*b* on the posterior face 2645 on each of the condyles 2632 extend from the posterior face 2645 towards the distal face 2643. Reinforcing keels 2670*a* and 2670*b* are substantially centered between the medial and lateral sides of the condyles 2632, but in alternative embodiments may be positioned in other positions or orientations. Reinforcing keel 2670*c* on the anterior face 2641 extends from the anterior face 2641 towards the distal face 2643. In the embodiment shown, reinforcing keel 2670*c* is substantially centered between the medial and lateral sides of the anterior face 2641, but in alternative embodiments may be positioned in other positions or orientations.

Figure 27A:
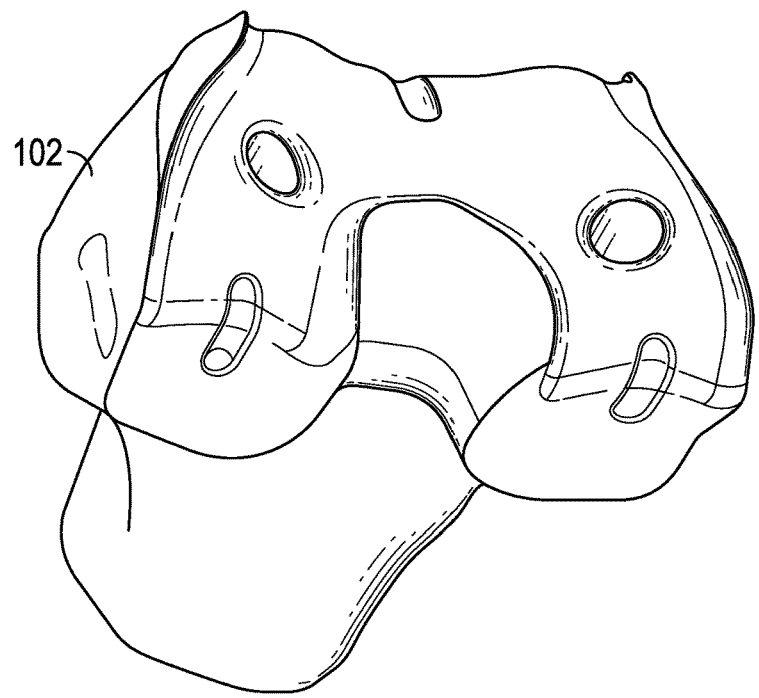
FIG. 27A illustrates a perspective view of a distal femur prepared to receive a femoral component according to an exemplary embodiment.
Figure 27B:
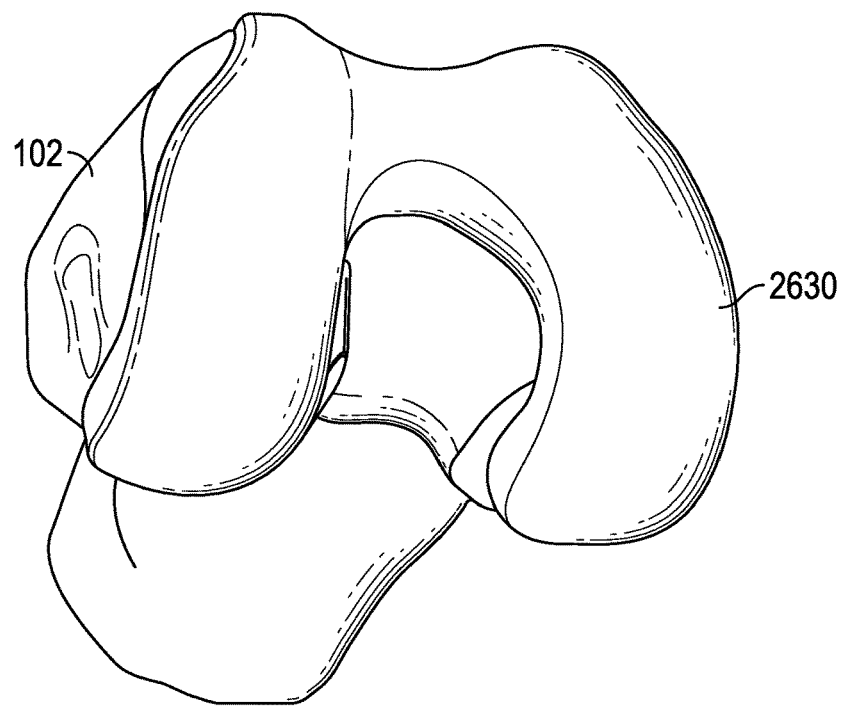
FIG. 27B illustrates a perspective view of a distal femur having an exemplary femoral component attached thereto.

Femur 102 may be resected to receive femoral component 2630 as shown in FIG. 27A. As shown, femur 102 has been prepared using one or more bone tools to match the configuration of interface surface 2635*b* of femoral component 2630. FIG. 27B shows femoral component 2630 positioned on femur 102.

As shown in the figures, femoral components according to the present invention can include various combinations of the features and configurations as disclosed above. Though certain combinations are shown in the exemplary embodiments provided, it should be understood that any of the disclosed femoral components, interface surfaces, elongated projections, trial projections, half pegs, and/or reinforcing keels may be used in combination with one another, and such combinations are contemplated in the present disclosure.

A method of implanting a femoral component according to the exemplary embodiments may include selecting a prosthetic component having a prosthetic body portion including a bearing surface and an interface surface. The interface surface, as discussed above, is configured to face a resected surface of a bone prepared to receive the prosthetic component. Then, using cutting tools, portions of the bones may be removed to form the resected surface of the bone, which is configured to match a counterpart portion of the interface surface of the prosthetic component.

Figure 28:
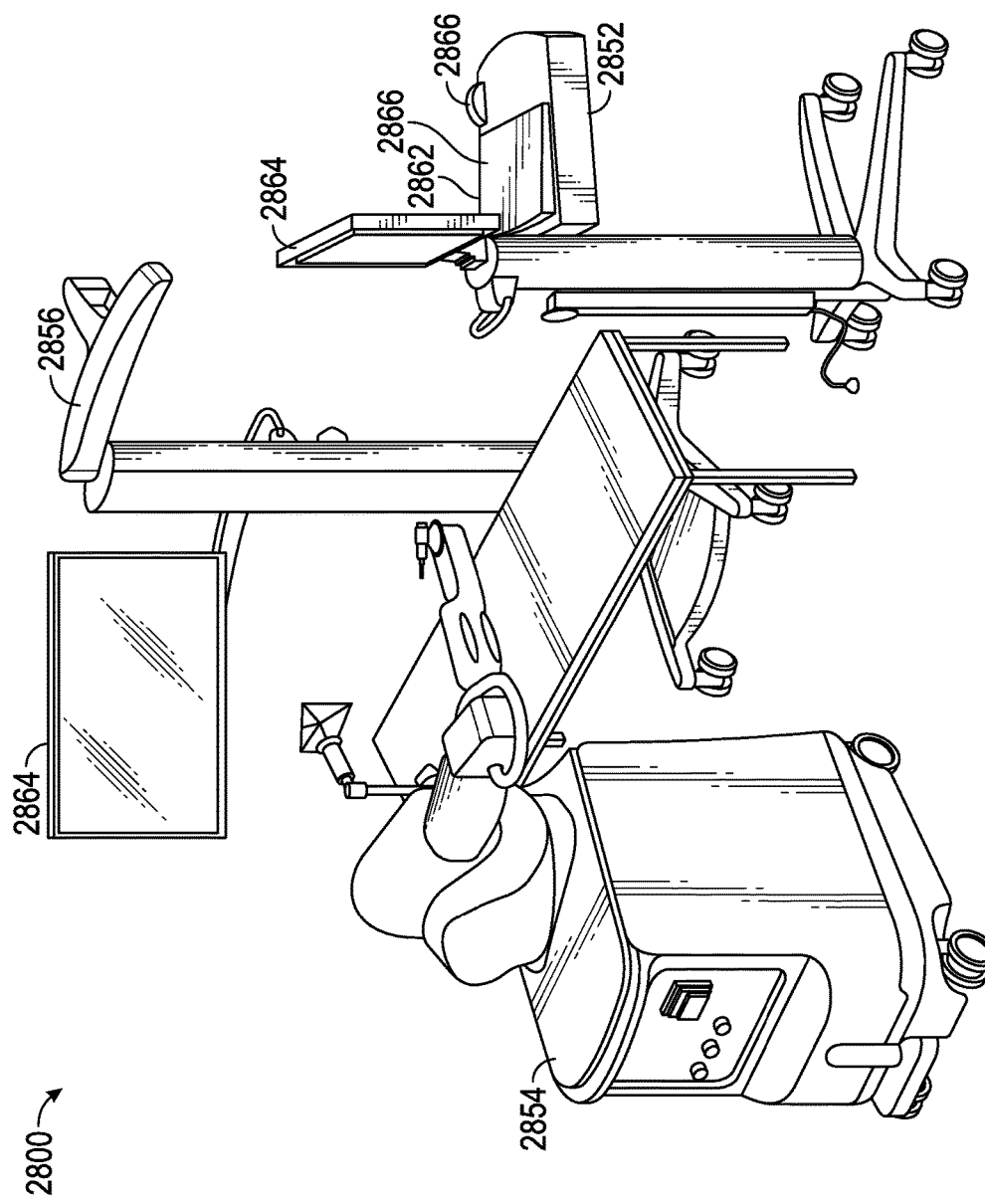
FIG. 28 illustrates a perspective view of an embodiment of a surgical system according to an exemplary embodiment.

The preparation of the bone, including removal of the bone, such as the distal femur, to receive the femoral components as described herein may be implemented using a robotic surgical system such as the RIO® Robotic Arm Interactive Orthopedic System available from MAKO Surgical Corp., Ft. Lauderdale, Fla. FIG. 28 shows an embodiment of an exemplary surgical system 2800 in which and for which the techniques described above can be implemented. The surgical system 2800 includes a computing system 2852, a feedback mechanism such as haptic device 2854 which may carry the surgical tool, such as a cutting tool, and a tracking system 2856. In operation, the surgical system 2800 enables comprehensive, intraoperative surgical planning including planning bone preparation procedures and performing bone preparation. The surgical system 2800 may also provide haptic guidance to a user (e.g., a surgeon) and/or limits the user's manipulation of the haptic device 2854 as the user performs a surgical procedure. The computing system 2852 may be programmed to determine control parameters based on data representative of a patient's anatomy (e.g., preoperative CT image data, ultrasound data); a virtual (or haptic) object associated with (or registered to) the anatomy; a parameter relative to the anatomy (e.g., a depth defined with respect to a portion of the anatomy); and/or the anatomy. The computing system 2852 can control the feedback mechanism, such as haptic device 2854 to generate a force, a torque, and/or vibration based on the position of the tool relative to the virtual object, the parameter, and/or the anatomy. In this way, surgical system 2800 can aid a user to plan or perform bone preparation to receive a prosthetic component according to one or more of the exemplary embodiments.

Embodiments of the subject matter, the methods, and the operations described in this specification can be implemented in digital electronic circuitry, or in computer software embodied on a tangible medium, firmware, or hardware, including the structures disclosed in this specification and their structural equivalents, or in combinations of one or more of them. In the embodiment of FIG. 28, the computing system 2852 may include hardware and software for operation and control of the surgical system 2800. Such hardware and/or software is configured to enable the system 2800 to perform the techniques described herein. The computing system 2852 includes a surgical controller 2862, a display device 2864, and an input device 2866.

The surgical controller 2862 may be any known computing system but is preferably a programmable, processor-based system. For example, the surgical controller 2862 may include a microprocessor, a hard drive, random access memory (RAM), read only memory (ROM), input/output (I/O) circuitry, and any other known computer component. The surgical controller 2862 is preferably adapted for use with various types of storage devices (persistent and removable), such as, for example, a portable drive, magnetic storage, solid state storage (e.g., a flash memory card), optical storage, and/or network/Internet storage. The surgical controller 2862 may comprise one or more computers, including, for example, a personal computer or a workstation operating under a suitable operating system and preferably includes a graphical user interface (GUI).

Figure 29:
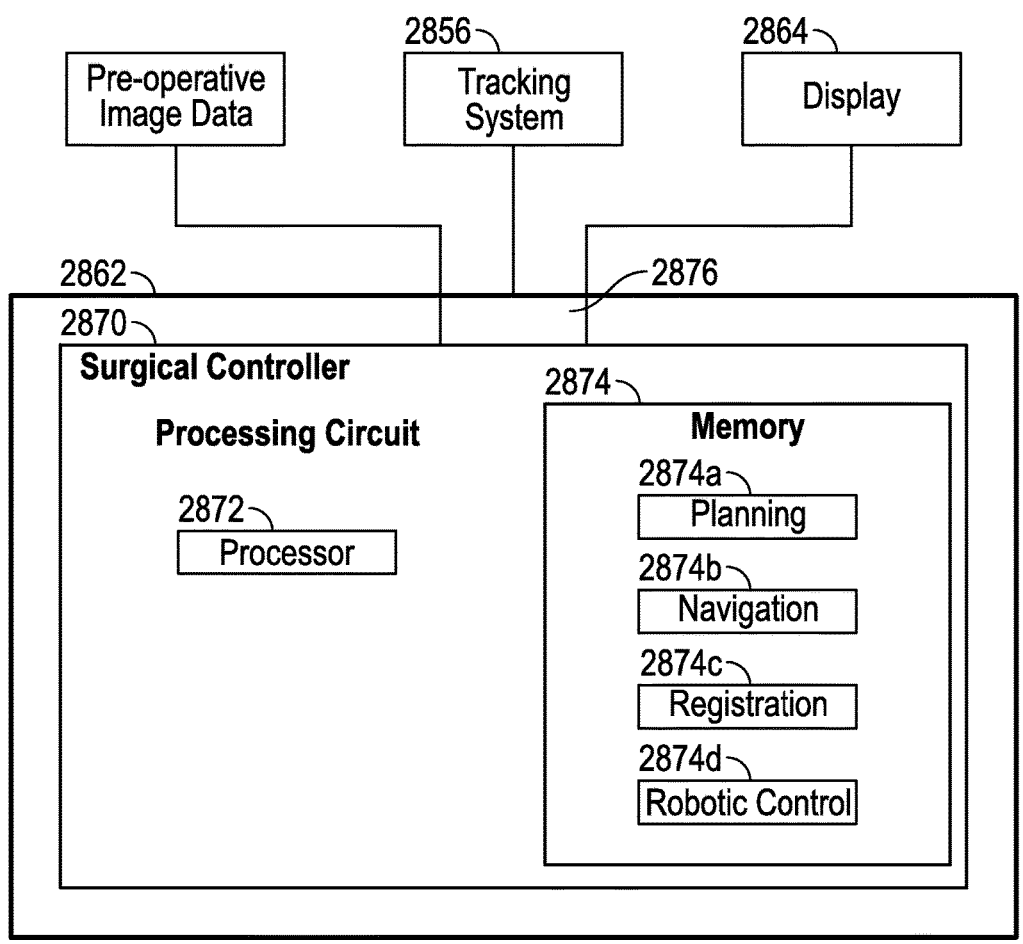
FIG. 29 illustrates a block diagram of a model surgical system according to an exemplary embodiment.

Referring to FIG. 29, in an exemplary embodiment, the surgical controller 2862 includes a processing circuit 2870 having a processor 2872 and memory 2874. Processor 2872 can be implemented as a general purpose processor executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit), a group of processing components, or other suitable electronic processing components. Generally, a processor will receive instructions and data from a read only memory or a random access memory or both. Memory 2874 (e.g., memory, memory unit, storage device, etc.) comprises one or more devices (e.g., RAM, ROM, Flash-memory, hard disk storage, etc.) for storing data and/or computer code for completing or facilitating the various processes described in the present application. Memory 2874 may be or include volatile memory or non-volatile memory. Memory 2874 may include database components, object code components, script components, or any other type of information structure for supporting the various activities described in the present application. According to an exemplary embodiment, memory 2874 is communicably connected to processor 2872 and includes computer code for executing one or more processes described herein. The memory 2874 may contain a variety of modules, each capable of storing data and/or computer code related to specific types of functions. In one embodiment, memory 2874 contains several modules related to surgical procedures, such as a planning module 2874a, a navigation module 2874b, a registration module 2874c, and a robotic control module 2874d.

Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). Accordingly, the computer storage medium may be tangible and non-transitory.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an embodiment of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Referring to the embodiment of surgical controller 2862 depicted in FIG. 29, the surgical controller 2862 further includes a communication interface 2876. The communication interface 2876 of the computing system 2852 is coupled to a computing device (not shown) of the haptic device 2854 via an interface, to the tracking system 2856 via an interface, and to the display 2864 through an interface. Through the communication interface 2876, pre-operative image data 2880 may also be received from an imaging system. The interfaces can include a physical interface and a software interface. The physical interface of the communication interface 2876 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). The software interface may be resident on the surgical controller 2862, the computing device (not shown) of the haptic device 2854, and/or the tracking system 2856. In some embodiments, the surgical controller 2862 and the computing device (not shown) are the same computing device. The software may also operate on a remote server, housed in the same building as the surgical system 2800, or at an external server site.

Computer system 2852 also includes display device 2864. The display device 2864 is a visual interface between the computing system 2852 and the user. The display device 2864 is connected to the surgical controller 2862 and may be any device suitable for displaying text, images, graphics, and/or other visual output. For example, the display device 2864 may include a standard display screen (e.g., LCD, CRT, OLED, TFT, plasma, etc.), a touch screen, a wearable display (e.g., eyewear such as glasses or goggles), a projection display, a head-mounted display, a holographic display, and/or any other visual output device. The display device 2864 may be disposed on or near the surgical controller 2862 (e.g., on the cart as shown in FIG. 28) or may be remote from the surgical controller 2862 (e.g., mounted on a stand with the tracking system 2856). The display device 2864 is preferably adjustable so that the user can position/reposition the display device 2864 as needed during a surgical procedure. For example, the display device 2864 may be disposed on an adjustable arm (not shown) or to any other location well-suited for ease of viewing by the user. As shown in FIG. 28 there may be more than one display device 2864 in the surgical system 2800.

The display device 2864 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), constraint data (e.g., axes, articular surfaces, etc.), representations of implant components, digital or video images, registration information, calibration information, patient data, user data, measurement data, software menus, selection buttons, status information, and the like.

In addition to the display device 2864, the computing system 2852 may include an acoustic device (not shown) for providing audible feedback to the user. The acoustic device is connected to the surgical controller 2862 and may be any known device for producing sound. For example, the acoustic device may comprise speakers and a sound card, a motherboard with integrated audio support, and/or an external sound controller. In operation, the acoustic device may be adapted to convey information to the user. For example, the surgical controller 2862 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a tone to indicate that a surgical cutting tool is nearing a critical portion of soft tissue.

To provide for other interaction with a user, embodiments of the subject matter described in this specification can be implemented on a computer having input device 2866 that enables the user to communicate with the surgical system 2800. The input device 2866 is connected to the surgical controller 2862 and may include any device enabling a user to provide input to a computer. For example, the input device 2866 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. For example, input device 2866 can allow the user to provide input to adjust the surgical plan. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The system 2800 also includes a tracking (or localizing) system 2856 that is configured to determine a pose (i.e., position and orientation) of one or more objects during a surgical procedure to detect movement of the object(s). For example, the tracking system 2856 may include a detection device that obtains a pose of an object with respect to a coordinate frame of reference of the detection device. As the object moves in the coordinate frame of reference, the detection device tracks the pose of the object to detect (or enable the surgical system 2800 to determine) movement of the object. As a result, the computing system 2852 can capture data in response to movement of the tracked object or objects. Tracked objects may include, for example, tools/instruments, patient anatomy, implants/prosthetic devices, and components of the surgical system 2800. Using pose data from the tracking system 2856, the surgical system 2800 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the surgical controller 2862 and/or the computer device of the haptic device 2854. For example, utilizing pose data from the tracking system 2856, the surgical system 2800 is able to associate the physical anatomy, such as the patient's femur, with a representation of the anatomy (such as an image displayed on the display device 2864). Based on tracked object and registration data, the surgical system 2800 may determine, for example, a spatial relationship between the image of the anatomy and the relevant anatomy.

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). The computing system 2852 may also include a coordinate transform process for mapping (or transforming) coordinates in one space to those in another to achieve spatial alignment or correspondence. For example, the surgical system 2800 may use the coordinate transform process to map positions of tracked objects (e.g., patient anatomy, etc.) into a coordinate system used by a process running on the computer of the haptic device 2854 and/or the surgical controller 2862. As is well known, the coordinate transform process may include any suitable transformation technique, such as, for example, rigid-body transformation, non-rigid transformation, affine transformation, and the like.

The tracking system 2856 may be any tracking system that enables the surgical system 2800 to continually determine (or track) a pose of the relevant anatomy of the patient. For example, the tracking system 2856 may include a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers.

The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

The haptic device 2854 may be the Tactile Guidance System™ (TGS™) manufactured by MAKO Surgical Corp., and used to prepare the surface of the patient's bone for insertion of the femoral component. The haptic device 2854 provides haptic (or tactile) guidance to guide the surgeon during a surgical procedure. The haptic device is an interactive surgical device, such as a robotic arm, that holds a surgical tool (e.g., a surgical burr) and is manipulated by the surgeon to perform a procedure on the patient, such as cutting a surface of a bone in preparation for femoral component installation. As the surgeon manipulates the robotic arm to move the tool and sculpt the bone, the haptic device 2854 guides the surgeon by providing force feedback that constrains the tool from penetrating a virtual boundary.

The construction and arrangement of the systems and methods as shown in the various exemplary embodiments are illustrative only. Although only a few embodiments have been described in detail in this disclosure, many modifications are possible. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A femoral prosthetic component, comprising:
a patellar guide portion;
a pair of condyles projecting from the patellar guide portion and forming an intercondylar notch therebetween;
a bearing surface; and
an interface surface, opposite the bearing surface, configured to face and engage a resected surface of a femur,
wherein the interface surface comprises an anterior face, a posterior face, a substantially curved surface between the anterior face and posterior face, and a pair of planar distal portions located at opposite sides of the intercondylar notch,
wherein the substantially curved surface extends between the anterior face and posterior face and extends proximally along a portion of the posterior face,
wherein a portion of the bearing surface curves inward toward the interface surface to form a median groove,
wherein the interface surface comprises a convexly raised canopy portion to accommodate the median groove, the convexly raised canopy portion forming a portion of the substantially curved surface,
wherein an intersection between the canopy portion and the anterior face is curvilinear,
wherein an intersection between the canopy portion and at least an anterior edge of the intercondylar notch is curvilinear, wherein each planar distal portion comprises a curved perimeter at least partially defined by an intersection between the curved surface and the planar distal portion, wherein a peg extends from each planar distal portion for insertion into the femur and the perimeter extends partially about the peg, and wherein the interface surface of the femoral prosthetic component is sized and contoured such that preparation of the femur to match the interface surface results in minimal resection of a distal portion of the femur.

2. The femoral prosthetic component of claim 1, wherein each planar distal portion is configured to abut a flat cut portion in the resected surface of the femur.

3. The femoral prosthetic component of claim 1, wherein each planar distal portion of the interface surface is a distal flat on the curved surface of the interface surface.

4. The femoral prosthetic component of claim 1, wherein each peg is configured to engage with a hole prepared in the femur.

5. The femoral prosthetic component of claim 1, wherein the interface surface comprises a first surface segment comprising a planar surface and a second surface segment comprising a non-planar surface.

6. The femoral prosthetic component of claim 1, wherein the anterior face define an anterior and posterior extent of the interface surface.

7. The femoral prosthetic component of claim 1, wherein the anterior face and posterior face each being planar and extending in an inferior-superior direction.

* * * * *